United States Patent
Collins, Sr. et al.

(10) Patent No.: US 10,241,014 B2
(45) Date of Patent: Mar. 26, 2019

(54) INSTRUMENT FOR ANALYTICAL SAMPLE PREPARATION

(71) Applicant: CEM Corporation, Matthews, NC (US)

(72) Inventors: Michael J. Collins, Sr., Matthews, NC (US); Joseph J. Lambert, Charlotte, NC (US); Matthew N. Beard, Huntersville, NC (US); Paul C. Elliott, Charlotte, NC (US)

(73) Assignee: CEM Corporation, Matthews, NC (US)

( * ) Notice: Subject to any disclaimer, the term of this patent is extended or adjusted under 35 U.S.C. 154(b) by 0 days.

(21) Appl. No.: 15/644,938

(22) Filed: Jul. 10, 2017

(65) Prior Publication Data

US 2019/0011338 A1    Jan. 10, 2019

(51) Int. Cl.
  *G01N 1/00*    (2006.01)
  *G01N 1/40*    (2006.01)
  (Continued)

(52) U.S. Cl.
  CPC .......... *G01N 1/4055* (2013.01); *B01L 3/5082* (2013.01); *B01L 7/52* (2013.01); *B01L 9/06* (2013.01); *G01N 1/4022* (2013.01); *G01N 1/4077* (2013.01); *G01N 35/0099* (2013.01); *G01N 35/026* (2013.01);
  (Continued)

(58) Field of Classification Search
  CPC ....................................................... G01N 1/44
  See application file for complete search history.

(56) References Cited

U.S. PATENT DOCUMENTS 2,643,940 A    6/1953 Stevens
4,265,860 A    5/1981 Jennings
(Continued)

FOREIGN PATENT DOCUMENTS

AU    2018204538    8/2018
CN    106018016    10/2016
(Continued)

OTHER PUBLICATIONS

Richter DE et al., Anal Chem 1996, 68, 1033.
(Continued)

*Primary Examiner* — Jyoti Nagpaul
(74) *Attorney, Agent, or Firm* — Philip Summa

(57) ABSTRACT

An instrument for extraction based molecular sample preparation and related processes is disclosed. The instrument includes a thermally conductive pressure resistant heating chamber and a thermally conductive sample cup positioned in the thermally conductive pressure resistant healing chamber for heating liquids and solids together in the thermally conductive sample cup. A liquid delivery inlet fixture in the thermally conductive pressure resistant heating chamber delivers liquids (solvent) from a supply to the thermally conductive sample cup in the thermally conductive pressure resistant heating chamber, and a chiller in liquid communication with the thermally conductive sample cup in the thermally conductive pressure resistant heating chamber receives heated liquids from the thermally conductive pressure resistant heating chamber when the chamber is opened to atmospheric pressure.

6 Claims, 23 Drawing Sheets

(51) Int. Cl.
*G01N 35/00* (2006.01)
*G01N 35/02* (2006.01)
*B01L 7/00* (2006.01)
*B01L 3/00* (2006.01)
*B01L 9/06* (2006.01)

(52) U.S. Cl.
CPC ............. *B01L 2300/0681* (2013.01); *B01L 2300/0809* (2013.01); *B01L 2300/0832* (2013.01); *B01L 2300/1805* (2013.01); *G01N 2001/4033* (2013.01); *G01N 2001/4061* (2013.01); *G01N 2001/4088* (2013.01); *G01N 2001/4094* (2013.01)

(56) References Cited

U.S. PATENT DOCUMENTS

| | | |
|---|---|---|
| 4,429,049 A | 1/1984 | Rogers |
| 5,017,500 A | 5/1991 | Langer |
| 5,268,103 A | 12/1993 | Jameson |
| 5,272,094 A | 12/1993 | Barker |
| 5,344,571 A | 9/1994 | Mendershausen |
| 5,447,077 A | 9/1995 | Lautenschlager |
| 5,601,707 A | 2/1997 | Clay |
| 5,620,659 A | 4/1997 | Revesz |
| 5,653,885 A | 8/1997 | Jameson |
| 5,660,727 A | 8/1997 | Gleave |
| 5,750,008 A | 5/1998 | Lautenschlager |
| 5,785,856 A | 7/1998 | Gleave |
| 5,858,178 A | 1/1999 | Lautenschlager |
| 5,932,095 A | 8/1999 | Walters |
| 6,048,457 A | 4/2000 | Kopaciewicz |
| 6,086,767 A | 7/2000 | Walters |
| 6,221,655 B1 | 4/2001 | Fung |
| 6,794,127 B1 | 9/2004 | Lafferty |
| 6,803,237 B2 * | 10/2004 | Manganini ............. B01D 61/18 219/710 |
| 8,569,072 B2 | 10/2013 | Halverson |
| 8,901,471 B2 | 12/2014 | Visinoni |
| 9,574,799 B2 | 2/2017 | Buese |
| 9,739,692 B2 | 8/2017 | Srinivasan |
| 2007/0275445 A1 | 11/2007 | De Bont |
| 2011/0005932 A1 | 1/2011 | Jovanovich |
| 2011/0233203 A1 | 9/2011 | Visinoni |
| 2013/0233093 A1 | 9/2013 | Pohl |
| 2013/0316466 A1 | 11/2013 | Srinivasan |
| 2013/0337132 A1 | 12/2013 | Fenna |
| 2014/0114084 A1 | 4/2014 | Hamler |
| 2014/0193303 A1 | 7/2014 | Ellis |
| 2015/0119592 A1 | 4/2015 | Hamler |
| 2015/0258521 A1 | 9/2015 | McAdams |
| 2016/0303490 A1 | 10/2016 | Ellis |
| 2016/0370035 A1 | 12/2016 | Hofer |
| 2016/0370357 A1 | 12/2016 | Lucas |

FOREIGN PATENT DOCUMENTS

| | | |
|---|---|---|
| CN | 107831252 | 3/2018 |
| DE | 2250933 | 5/1974 |
| EP | 0932355 | 8/1999 |
| EP | 2371437 | 10/2011 |
| EP | 3072568 | 9/2016 |
| FR | 2196831 | 3/1974 |
| GB | 380954 | 9/1932 |
| GB | 477567 | 1/1938 |
| GB | 530345 | 12/1940 |
| GB | 613568 | 11/1948 |
| GB | 583121 | 11/1952 |
| GB | 776938 | 6/1957 |
| GB | 345131 | 8/1960 |
| GB | 1012545 | 12/1965 |
| GB | 1065720 | 4/1967 |
| GB | 1074231 | 7/1967 |
| GB | 1123847 | 8/1968 |
| JP | H08029432 | 2/1996 |
| JP | H08338832 | 12/1996 |
| JP | 2005214785 | 8/2005 |
| JP | 2016101166 | 6/2016 |
| WO | 9325842 | 12/1993 |
| WO | 9627417 | 9/1996 |
| WO | 2008101670 | 8/2008 |
| WO | 2015160419 | 10/2015 |
| WO | 2018148225 | 8/2018 |

OTHER PUBLICATIONS

Definitions of "adsorption," "organic," "solvent," and "sorbent"—Lewis, Hawley'S Condensed Chemical Dictionary, 15th Edition, 2007, John Wiley & Sons.
EPA Method 3545 Pressurized Fluid Extraction (PFE), Rev. 1, Jan. 1998; pp. 10.
Definitions of "adsorb," "loose," "opposite," "sorbent," and "solid,"—Urdang, The Random House College Dictionary, Random House Inc. (1972).
EPA Method 3540C—Soxhlet Extraction, Rev. 3, Dec. 1996, pp. 8.
EPA Method 3550C—Ultrasonic Extraction, Revision 3, Feb. 2007; pp. 17.
EPA Method 8270D—Semivolatile Organic Compouns by Gas Chromatography/Mass Spectrometry (GC/MS), Rev. 4, Jan. 1998, pp. 62.
CRM Catalog No. 727 Base/Neutrals & Acids in Soil, ERA Environmental 2014 Proficiency Testing and Reference Materials, Online Product Catalog, Waters Corporation.
Knowles, D; Dorich, B; Carlson, R; Murphy, B; Francis, E; Peterson, J, Richter, B. "Extraction of Phthalates from Solid Liquid Matrices," Dionex Corporation, 2011, pp. 4.
Consumer Products Safety Commission, Test Method: CPSC-CH-C1001-09.3 Standard Operating Procedure for Determination of Phthalates Apr. 1, 2010; http://www.cpsc.gov/about/cpsia/ CPSC-CH-C1001-09.3.
Safety Data Sheet: Phthalates from Polyethlene in a CRM sample; SPEX CertiPrep CRM-PE001; Metuchen, NJ 08840, 2017; pp. 7.
Arsenault, J.C. Beginner's Guide to SPE Solid-Phase Extraction; 2012, Waters Corporation; pp. 28.
Lehotay, et al., Comparison of QuEChERS sample preparation methods for the analysis of pesticide residues in fruits and vegetables; Journ of Chromatography A, 1217 (2010) 2548-2560.
Kabay et al, Solvent-impregnated resins (SIRS)—Methods of preparation and their applications; Reactive & Functional Polymers 70 (2010) 484-496.
QuEChERS Simplified, Waters Corporation, Jul. 2016, pp. 8.
Thei Basics: QuEChERS Step by Step; 2013, accessed Dec. 8, 2016 at http://blog.teledynetekmar.com/blog/bid/350968/The-Basics-QuEChERS-Step-by-Step.
AOAC Official Method 2007.01 Pesticide Residues in Food by Acetonitrile Extraction and Partitioning with Magnesium Sulfate, 2007 AOAC International, pp. 9.
Burns, Donald—Automated Sample Preparation, Anaytical Chemistry, vol. 53, No. 12, Oct. 1981.
Automated Protein and Peptide Sample Preparation for Mass Spec Analysis, Agilent Technologies, 2015, pp. 8.
Solid Phase Extraction, SPE Protocol—Sample Preparation; Orochem Technologies, Inc., 2016, pp. 5.
Co-pending U.S. Appl. No. 15/644,920 for "Rapid Sample Preparation for Analytical Analysis Using Dispersive Energized Extraction" filed Jul. 10, 2017.
Co-pending U.S. Appl. No. 15/644,950 for "Rapid Energized Dispersive Solid Phase Extraction (SPE) for Analytical Analysis" filed Jul. 10, 2017.
Frenich A.G. et al., "Determination of Pesticides in Food of Animal Origin" in Tadeo J.L. (Ed), "Analysis of Pestcides in Food and Environmental Samples," CRC Press, 2008, pp. 177-207.
Song, S. et al., "Development, comparison and application of sorbent-assisted accelerated solvent extraction, microwave-assisted extraction and ultrasonic-assisted extraction for the determinatioin of polybrominated diphenyl ethers in sediments," Journal of Chromatography A, 2016, vol. 1475, pp. 1-7.

(56) References Cited

OTHER PUBLICATIONS

How To Keep Grounds Out of Percolated Coffee_Percolator Coffee Pot [retrieved from internet on Jan. 11, 2018]<URL:https://web.archive.org/web/20160317210445/http://percolatorcoffeepot.org/how-to-keep-grounds-out-of-percolated-coffee/> published on Mar. 17, 2016 as per Wayback Machine.
Standard Operating Procedure for Soxhlet Extraction of Biomass; accessed Sep. 16, 2018 at https://pdfs.semanticscholar.org/presentation/a96a/47d960bfbcde1f908239ccfaa8fc9d006b22.pdf; 12 pages.
Refluxing a Reaction; accessed Sep. 26, 2018 at http://cactus.dixie.edu/smblack/chemlabs/refluxing_a_reaction.pdf,1 page.
Practical techniques in organic chemistry (Heating under reflux); accessed Sep. 21, 2018 at https://quizlet.com/137786055/161-practical-techniques-in-organic-chemistry-heating-under-reflex-flash-cards/; 2 pages.
Reflux and distillation posted Apr. 30, 2015 on ASSIST (Australian School Science Information Support for Teachers and Technicians); accessed Sep. 20, 2018 at https://assist.asta.edu.au/print/2802; 6 pages.
Ondruschka et al., Microwave-Assisted Extraction—A State-of-the-Art Overview of Varieties; Chimia 60 (2006); 321-325.
NEOS Microwave Soxhlet; Milestone brochure; date unknown; 6 pages.
Yunjie Ding et al., Determination of Pharmaceuticals in Biosolids using Accelerated Solvent Extraction and Liquid Chromatography/Tandem Mass Spectrometry; Journal of Chromatography A (2010); 24 pages.
ASE 200 Accelerated Solvent Extractor Operator's Manual, Doc. No. 031149, Rev. 4, Dec. 1999; 184 pages.
Jacketed vessels for all applications with flexibility to meet the most demanding design; AndersonDahlen Inc., Nov. 5, 2017; accessed Aug. 22, 2018 at https://web.archive.org/web/20171105035338/https://www.andersondahlen.com/components/vessels/jacketed-vessels.
"I use a moka pot to make coffee every morning. I get coffee beans from Starbucks and it tastes good but how can I make it taste even better?" Published Jan. 16, 2015 on Quora.com; accessed at: https://www.quora.com/I-use-a-moka-pot-to-make-coffee-every-morning-I-get-coffee-beans-from-Starbucks-and-it-tastes-good-but-how-can-I-make-it-taste-even-betterhttps://www.quora.com/.
Van Den Berg, C., In-situ product recovery from fermentation broths, 2010, Doctoral dissertation, TU Delft, Delft University of Technology, 117 pages.
Improved Soxhlet Extraction of Medical Marijuana Oil [viewed on internet on Jan 7, 2019] < URL: https://www.youtube.com/watch?V=XOLJp8G732g>, published on May 15, 2013.
"General extraction time and solvent type for soxhlet extraction—can anyone help?" [accessed Jan 7, 2019] < URL:https://www.researchgate.net/post/General-extraction_time_and_solvent_type_for_soxhlet_extraction_can_anyone_help>, published 2013.
Dionex ASE Extraction Thimbles, Thermo Scientific, 2014; 4 pages.

\* cited by examiner

INSTRUMENT FOR ANALYTICAL SAMPLE PREPARATION

RELATED APPLICATION

This application is related to application Ser. No. 15/644,920 filed concurrently herewith for Rapid Sample Preparation for Analytical Analysis Using Dispersive Energized Extraction and application Ser. No. 15/644,950 filed concurrently herewith for Rapid Energized Dispersive Solid Phase Extraction (SPE) for Analytical Analysis.

BACKGROUND

The present invention relates to analytical chemistry, and in particular relates to sample preparation for molecular analysis.

In order to carry out molecular analysis (the task of identifying one or more compounds in a sample) of any product, a sample of the product must be in such a form that it can be easily analyzed by chromatography, spectroscopy, mass spectroscopy and/or nuclear magnetic resonance instrumentation Because these analytical instruments require substantially pure isolated analytes, some intermediate slops, generally referred to as "sample preparation", must be carried out to isolate the compounds of interest from the sample matrix in which they might be found and prepare them for analysis by instrumentation.

The task of identifying one or more compounds in a sample—presents an enormously larger set of possibilities and challenges related to sample preparation. The number of "naturally occurring" compounds (those produced by plants or animals) is immeasurably large, and the capabilities of modern organic and inorganic synthesis have generated—figuratively or literally—a similar number of synthetic compounds.

There is tremendous interest in identification or quantitative measurement for compounds of interest as it relates to industrial processes, and for environmental testing for contaminants in waste water, soil, and air.

Even a small group of recognizable representative samples would include pesticides in food, other synthetic chemicals in food (antibiotics, hormones, steroids), synthetic compositions (benzene, toluene, refined hydrocarbons) in soil, and undesired compositions in everyday items (e.g., Bisphenol-A ("BPA") in polycarbonate bottles and other plastic food packaging.

In general extraction has been a main form of sample preparation; i.e., drawing one or more compounds of interest from a sample by mixing the sample with a solvent into which the desired compound(s) will be extracted from the sample so that it can be measured by an analytical technique.

For several generations (and continuing to date), sample preparation in the form of extraction has been carried out by the well-understood Soxhlet method which was invented in the 19th century. In the Soxhlet technique, a single portion of solvent circulates repeatedly through a sample matrix until extraction is complete. To the extent, the Soxhlet method has an advantage, it allows an extraction to continue on its own accord for as long as the boiling flask is heated and the condenser is cold.

This method of extraction can take hours to completely extract the compounds of interest. Other concerns of safely from flammable solvents, hazardous waste and breakable glassware are significant drawbacks to this method.

Another commonly known extraction method uses ultrasonication; i.e., the irradiation of a liquid sample with ultrasonic (>20 kHz) waves resulting in agitation. Although ultra-sonication has an advantage of speeding up the extraction process the disadvantages are that it is a labor intensive, manual process and uses large amounts of solvents.

In more recent years analytical scale microwave-assisted extraction (MAE) has been utilized. MAE uses microwave energy to heat solvents in contact with a sample in order to partition analytes from the sample matrix into the solvent. The main advantage of MAE is the ability to rapidly heat the sample solvent mixture. When using closed pressurized-vessels the extraction can be performed at elevated temperatures that accelerate the extraction of the compounds of interest from the sample matrix. MAE accelerates the extraction process, but has its disadvantages as well. In the microwave healing process typically a polar solvent is needed to provide dipole rotation and ionic conduction through reversals of dipoles and displacement of charged ions present in the solute and the solvent, limiting non-polar solvent use. MAE uses expensive, high-pressure vessels that do not provide a means of filtering the extract, and they must be cooled before pressure can be released.

In the 1990's automated apparatuses for the extract ion of analytes were developed. These apparatuses incorporated solvent extraction in pressurized cells under elevated temperatures and pressures and are referred to as "Pressurized Fluid Extraction" ("PFE") or "Accelerated Solvent Extraction" ("ASE"). PFE has shown to be similar to Soxhlet extraction, except that, the solvents are at elevated temperatures where they exhibit high extraction properties. This procedure was first developed by Dionex (Richter DE et al., Anal Chem 1996, 68, 1033). One such PFE automated extraction system (Dionex ASE) is commercially available.

PFE was initially used for environmental contaminants (EPA Method 3545, herbicides, pesticides, hydrocarbons) in soil, sediments and animal tissues but has expanded to use in foods, pharmaceutical products and other biological samples.

PFE provides an efficient extraction, but still has not overcome the major bottlenecks associated with the many steps necessary to prepare a sample for analysis. PFE utilizes multiple-component cells and many steps. The cells are tightly packed with the sample and other packing material to eliminate any void areas in the cell, enhance separation, and avoid channeling. Preparing a cell for analysis can typically take 15 minutes. The cells are pre-pressurized at pressures up to 1500 psi and heated up to 200° C. prior to adding the solvent. Extraction is based on chromatographic principles to force the hot solvent through the column. Cycle times can take up to 20 minutes and the requirements of high pressure lead to secondary disadvantages with respect to cost and maintenance.

Newer PSE or ASE techniques attempt to address some of these difficulties, but still require that the cells be tightly packed, adding to the complexity and overall time required for each extraction.

Sample preparation, although having developed over the years, nevertheless remains the major bottleneck in molecular analysis. Accordingly, although the Soxhlet, Ultrasonication, MAE and PFE techniques have their advantages, each remains relatively time-consuming. As a result, when multiple samples are required or desired to provide necessary or desired information, the time required to carry out any given extraction-based molecular preparation step reduces the number of samples that can be prepared in any given amount of time, thus reducing the amount of information available in any given time interval. To the extent that, measurements are helpful or necessary in a continuous process, this represents a longer gap between samples or before an anomalous or troublesome result can be identified.

In recent decades, advances in liquid chromatography have led to analogous uses of packed columns in a technique referred to as solid phase extraction ("SPE"). Originally, chromatography was used to separate fractions in mixed samples for analytical purposes, and indeed it still serves this purpose very very well.

In SPE, the chromatography technique is modified to extract an anal vie from a matrix. Nevertheless, SPE fundamentally remains liquid chromatography technique in which molecules spread out (travel at different speeds) within a column based on their polarity, the particle size and polarity of the packed column (stationary phase), the polarity of the flowing liquid (mobile phase), the size (length and diameter) of the column and specific factors such as "hold-up volume," "linear velocity," and "flow rate." See, e.g.. Arsenault, J. C. 2012. Beginner's Guide to SPE. Milford Mass.: Waters Corporation. (Arsenault 2012).

Although SPE is useful, it has limiting characteristics, some of which include the following factors. First, a proper description of SPE is "liquid-solid phase extraction" because the sample matrix that holds the analyte is almost always a liquid.

Second, because SPE is essentially a liquid chromatography technique, it requires either column packing steps or a new column for each test, along with a potential pre-swelling step depending upon the material selected or required for the stationary phase. SPE typically requires different methods and manipulative steps for different analytes.

Third a more deliberate (slower) flow through the packed column tends to produce belter separation among the fractions. Thus, in a very real sense slower SPE is better than faster SPE.

Finally, if an additional driving force (i.e., in addition to simple gravity flow) is required to move solvent through the SPE column, an external liquid or gas pump, or a centrifuge, or a vacuum pull must be incorporated, which in turn increases, to some lesser or greater amount, the complexity of the technique and any supporting systems.

More recently, a dispersive solid phase extraction ("dSPE") method referred to as "Quechers" or "QuEChERS" ("quick-easy-cheap-effective-rugged-safe") has become a standard for extraction preparation of molecular samples. Dispersive SPE addresses some of the disadvantages of SPE, but still requires an extraction step, the adjustment of pH with an appropriate ionic salt, is labor-intensive (even if advantageous compared to other methods), and requires two separate centrifuge steps.

Quechers is in many ways less complex than Soxhlet extraction, but still requires a multi-step process. In the literature, this is sometimes called a "three step process" (e.g., Paragraph 0153 of U.S. Patent Application Publication No. 20160370357), but in reality Quechers requires at least the following: homogenization of the matrix that contains the analyte of interest; adding extraction solvent; band agitation; buffering; a second agitation step; a centrifuge separation step; decanting; dispersive solid phase extraction ("dSPE") clean up; a second centrifuge separation step; and decanting the supernatant liquid following the centrifuge step.

In addition to the multi-step handling and transfer of the solvent, the sample, and the various mixtures, each of the centrifuge steps takes a recommended five minutes; so that the full Quechers sample preparation takes at least about 15-20 minutes.

Accordingly, although the Soxhlet, SPE, and Quechers (dSPE) methods have their advantages, each remains relatively time-consuming. As a result, when multiple samples are required or desired to provide necessary or desired information, the time required to carry out any given extraction-based molecular preparation step reduces the number of samples that can be prepared in any given amount of time, thus reducing the amount of information available in any given time interval. To the extent that measurements are helpful or necessary in a continuous process, this represents a longer gap between samples or before an anomalous or troublesome result can be identified.

In summary, among other disadvantages current sample preparation techniques are slow, require a large number of separate steps, use excess solvent, are difficult to automate, and operate under high liquid pressure.

Accordingly, a need continues to exist for efficient rapid extraction-based molecular preparation techniques.

SUMMARY

In one aspect the invention is a combination for solvent extraction. The combination includes a heated, pressure-sealed reaction chamber, a sample cup in the reaction chamber, the sample cup including one open filtered end and a mouth opposite the open filtered end, an extraction sample in the sample cup, and an extraction solvent inside the sample cup and outside the sample cup between the exterior of the sample cup and the interior of the reaction chamber.

In one aspect, the invention is an instrument for extraction based molecular sample preparation and related processes. The instrument includes a thermally conductive pressure resistant heating chamber with a pressure resistant chamber closure. A sample cup is positioned in the thermally conductive pressure resistant heating chamber and for heating liquids and solids together in the sample cup. A liquid delivery inlet fixture communicates with the thermally conductive pressure resistant heating chamber for delivering liquids (solvent) from a supply to the sample cup in the thermally conductive pressure resistant heating chamber. A gas delivery head in communication with the thermally conductive pressure resistant heating chamber is positioned at or near the bottom of the sample cup for delivering an inert gas from a supply to the sample cup to agitate the contents of the sample cup. A chiller is in liquid communication with the sample cup in the thermally conductive pressure resistant heating chamber for receiving heated liquids from the thermally conductive pressure resistant healing chamber when the chamber is opened to atmospheric pressure.

In yet another aspect, the invention is an instrument for extraction based molecular sample preparation and related processes that includes a plurality of sample cups and a plurality of collection vials carried in a common rack, a robot arm for moving one of the sample cups from (to and from in practice) the rack into an opened pressure chamber, a pressure resistant chamber closure that reciprocates vertically to open and close the pressure chamber, a liquid inlet fixture for delivering liquids to the pressure chamber when the pressure chamber is closed, a heater for raising the temperature of liquids in the pressure chamber when the pressure chamber is closed, a gas inlet fixture for delivering an agitating gas flow to the pressure chamber when the pressure chamber is closed, and a drain for releasing liquids front the pressure chamber under pressure generated by delivered heated liquids in the chamber.

In yet another aspect, the invention is a sample preparation instrument that includes an sample cup with one opened filtered end and a mouth opposite the filtered end. A reaction chamber surrounds the sample cup so that the reaction chamber and the sample cup define open jacket portions between the interior surfaces of the reaction chamber and exterior surfaces of the sample cup. The reaction chamber includes a drain floor in communication with the opened filtered end of the sample cup, a pressure sealing lid over the mouth of the sample cup, a first solvent inlet from the pressure sealing lid to the interior of the sample cup; and a second solvent inlet from the drain floor into the reaction chamber. A reaction chamber heater is in thermal contact with the reaction chamber so that solvent can be added from both of the first and second solvent inlets into the sample cup and from the second solvent inlet into the jacket portions so that the heater can heat the reaction chamber and solvent in the jacket portions, and so that heated solvent in the jacket portions can heat the sample cup and heat solvents and extraction samples inside the sample cup and so that solvent from the second inlet can enter the sample cup through the open filtered end and favorably agitate extraction solvents and samples in the sample cup.

The foregoing and other objects and advantages of the invention and the manner in which the same are accomplished will become clearer based on the followed detailed description taken in conjunction with the accompanying drawings.

DETAILED DESCRIPTION

In general, terms are used herein in a manner that is clear from the context of this specification, or as explicitly stated, or using standard English dictionary definitions.

The term "solvent" is used in its well understood chemical sense; e.g., "a substance capable of dissolving another substance (solute) to form a uniformly dispersed mixture (solution) at the molecular or ionic size level." The adjective "organic" is used in its well understood sense to "embrace all compounds of carbon" other than certain small molecule combinations of carbon with oxygen, sulfur, and metals, and in some cases halogens. See, Lewis, Hawley's Condensed Chemical Dictionary, 15th Edition, 2007, John Wiley & Sons The "sample matrix" is the material to be tested for the presence and optionally the amount of analyte.

The "analyte" is the molecular compound of interest.

The "solvent extract" is the solution of analyte in a solvent following extraction.

The "sample cup" is the container for the sample matrix and the solvent.

The "collection vessel" is the container that collects the solvent extract following cooling.

A "liquid sample matrix" is a sample in which the analyte is present in a liquid rather than a solid matrix.

Figure 1:
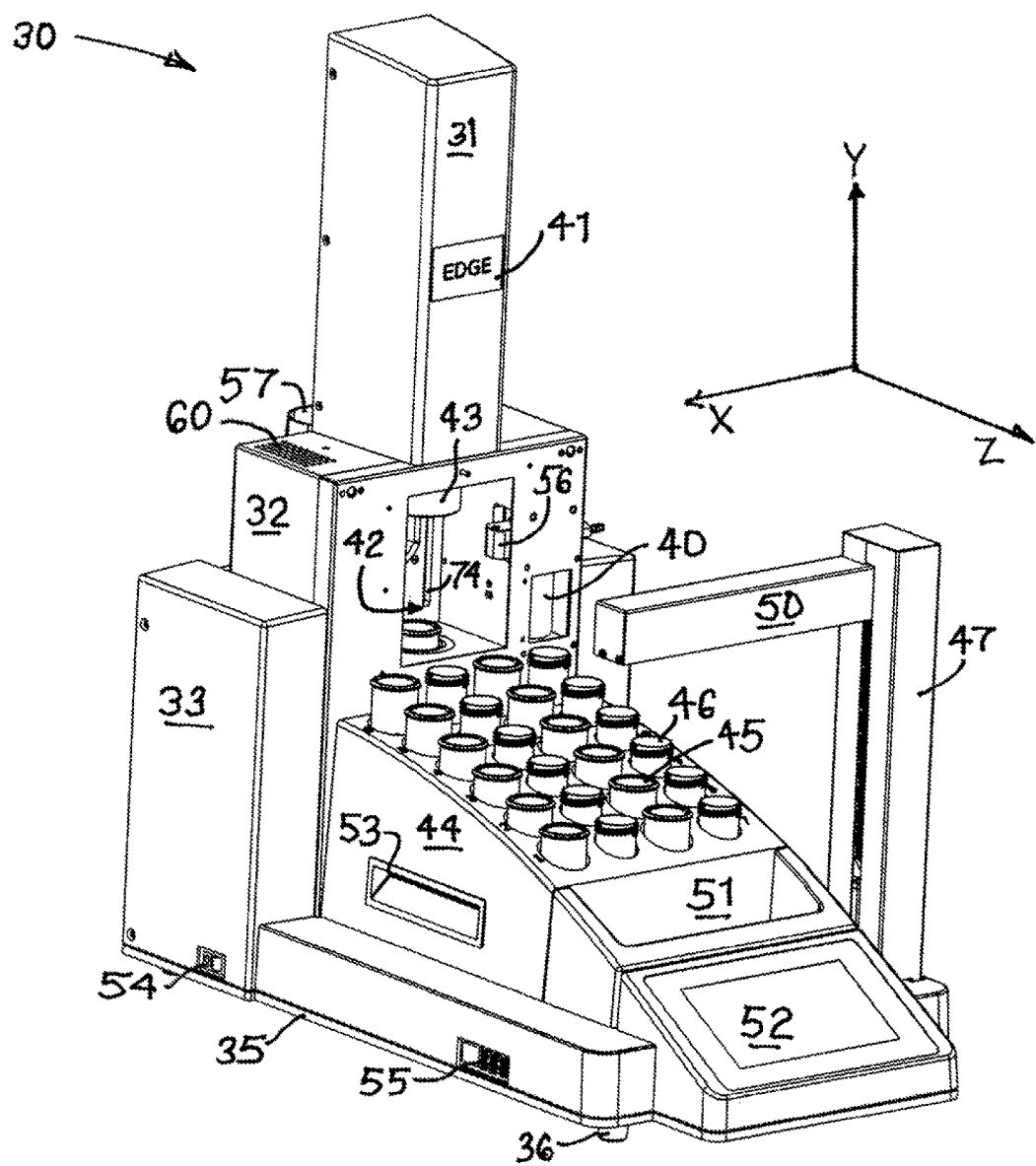
FIG. 1 is a front perspective view of an instrument according to the invention.

FIG. 1 is a front perspective view illustrating a number of elements of an exemplary instrument broadly designated at 30 for extraction based molecular sample preparation and related processes. FIG. 1 shows that the instrument includes an actuator housing 31, a chamber housing 32, a main housing 33, a base housing 34, and a base plate 35 resting on a plurality of feet 30. The illustrated embodiment also carries a name tag 41.

FIG. 1 also illustrates portions of a thermally conductive pressure resistant heating chamber broadly designated at 42 with a pressure resistant chamber closure broadly indicated at 43. A common rack 44 holds a plurality of sample cups 45 and a plurality of collection vials 46.

As used herein, the term "heat conductive" or "thermally conductive" are used in their well-understood sense to represent, materials through which heat passes relatively quickly. Its opposite is, of course, the term "insulating," which is likewise well-understood as describing materials through which heat passes more slowly. On that basis, many metals and alloys are particularly useful for the vessel given that such conductivity is one of the distinguishing characteristics of most metals and alloys. Alternatively, many polymeric materials are considered insulating and ordinarily less helpful in the context of the invention. The thermal conductivities of many metals and alloys are published and widely disseminated, and an appropriate metal or alloy can be selected by the skilled person without undue experimentation.

Figure 8:
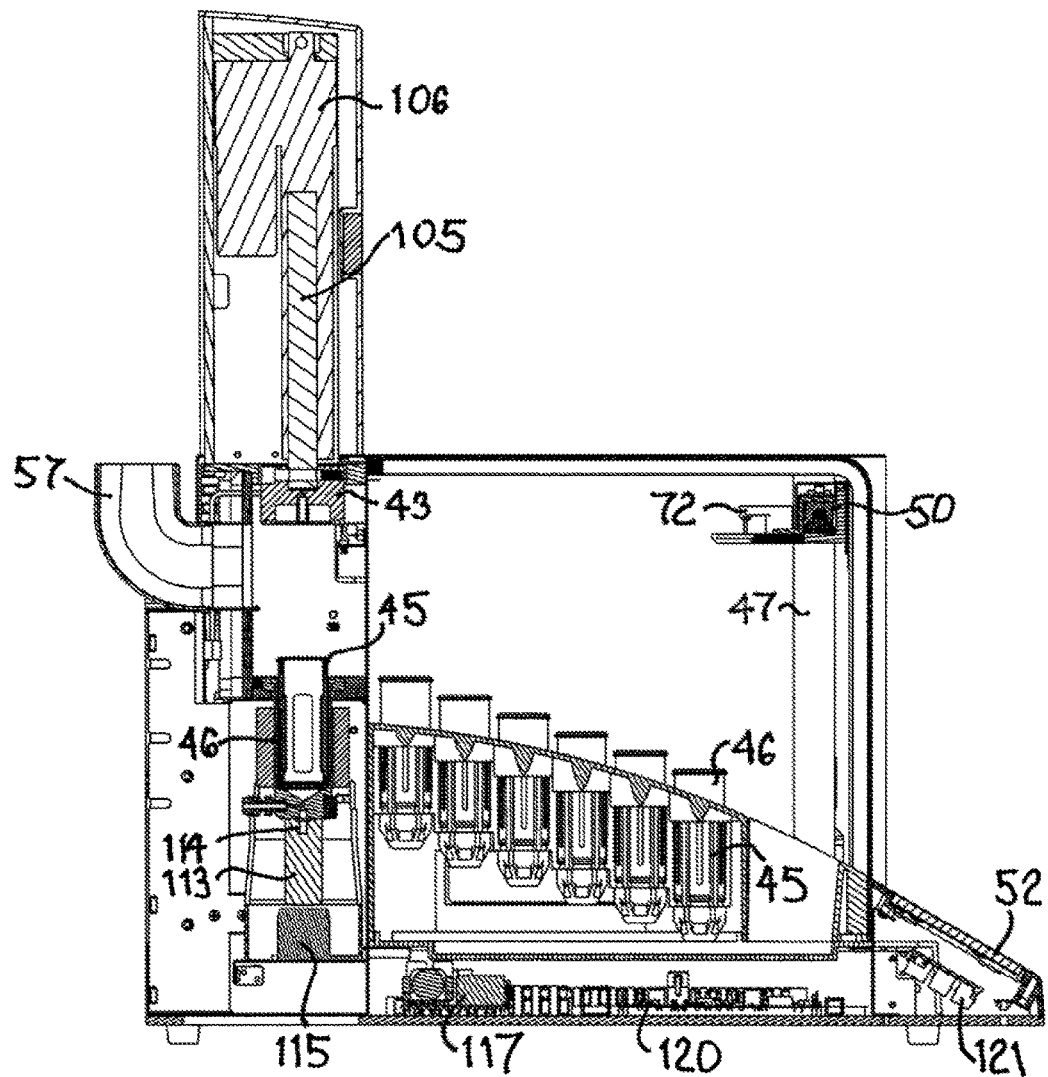
FIG. 8 is a cross-sectional view take them along lines 11-11 of FIG. 2.

A y-z axes robot arm 47 carries an x-axis robot arm 50. The robot arms 47, 50 are controlled by a processor (CPU FIG. 8) for the purpose of moving the sample cups (one at a time in the illustrated embodiment) to and from the common rack 44 into the opened pressure chamber 42. The robot arms 47, 50 also serve other functions with respect to the movement of fluids and the collection vials (FIG. 8).

Other aspects of the illustrated embodiment include the spill basin 51, the touch screen 52 for input and output to the processor, a transparent cover (not illustrated for the sake of clarity, a handle 53 on the rack 44, an on off switch 54 and communication ports 55. FIG. 1 also illustrates portion of a syringe 40 for certain fluid movements (FIG. 10) within the instrument. A flush fixture 56 is positioned within the chamber housing 32.

FIG. 1 also illustrates portions of a chamber exhaust 57 and a vent intake 60 for cooling some of the electronics within the chamber housing 32.

Figure 2:
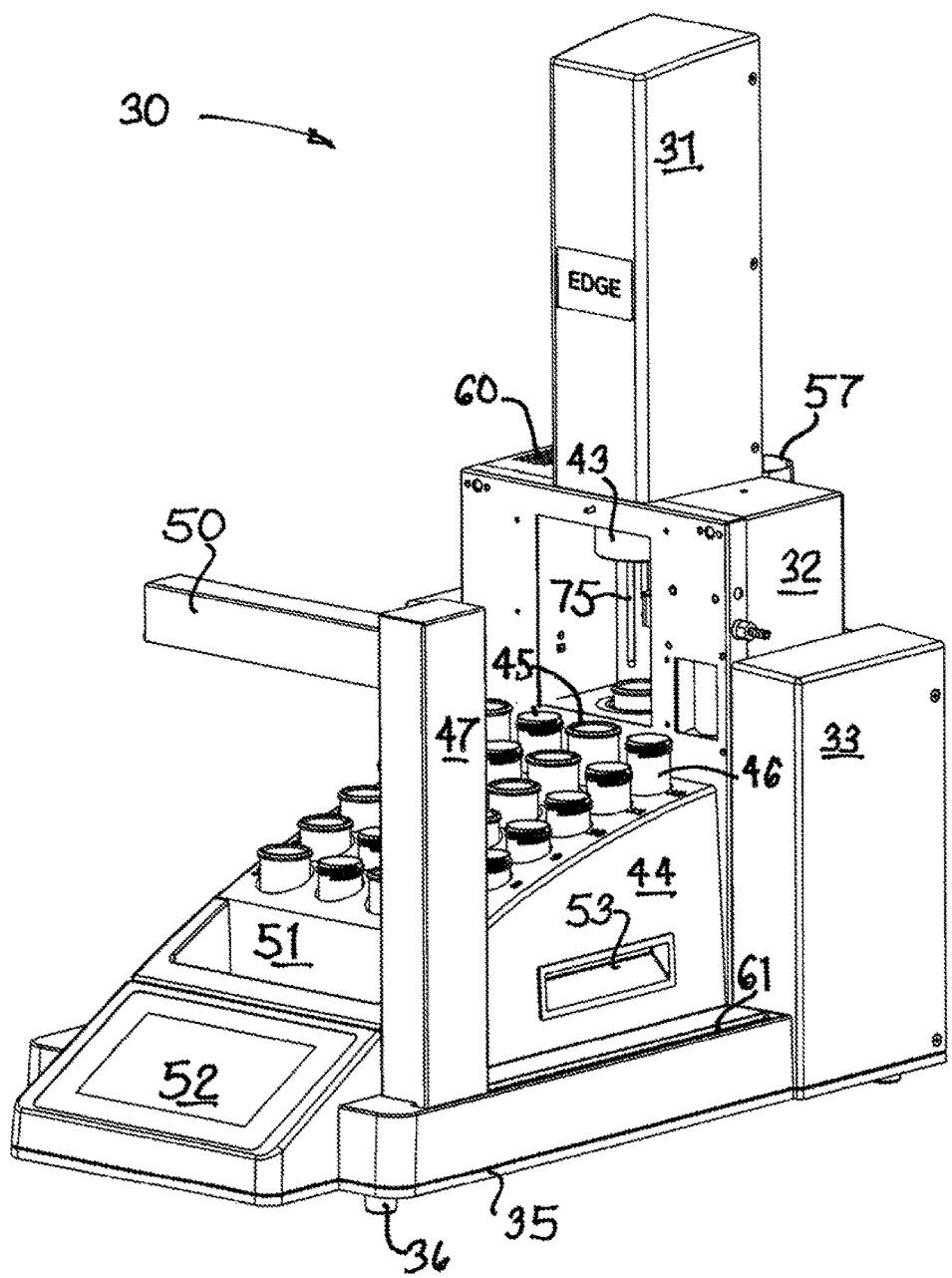
FIG. 2 is a second perspective view of an instrument according to the invention.

FIG. 2 is a perspective view similar to FIG. 1, but showing some slightly different details such as the second fluid head slot 75 and the track 61 for the y-z robot arm 47.

Figure 3:
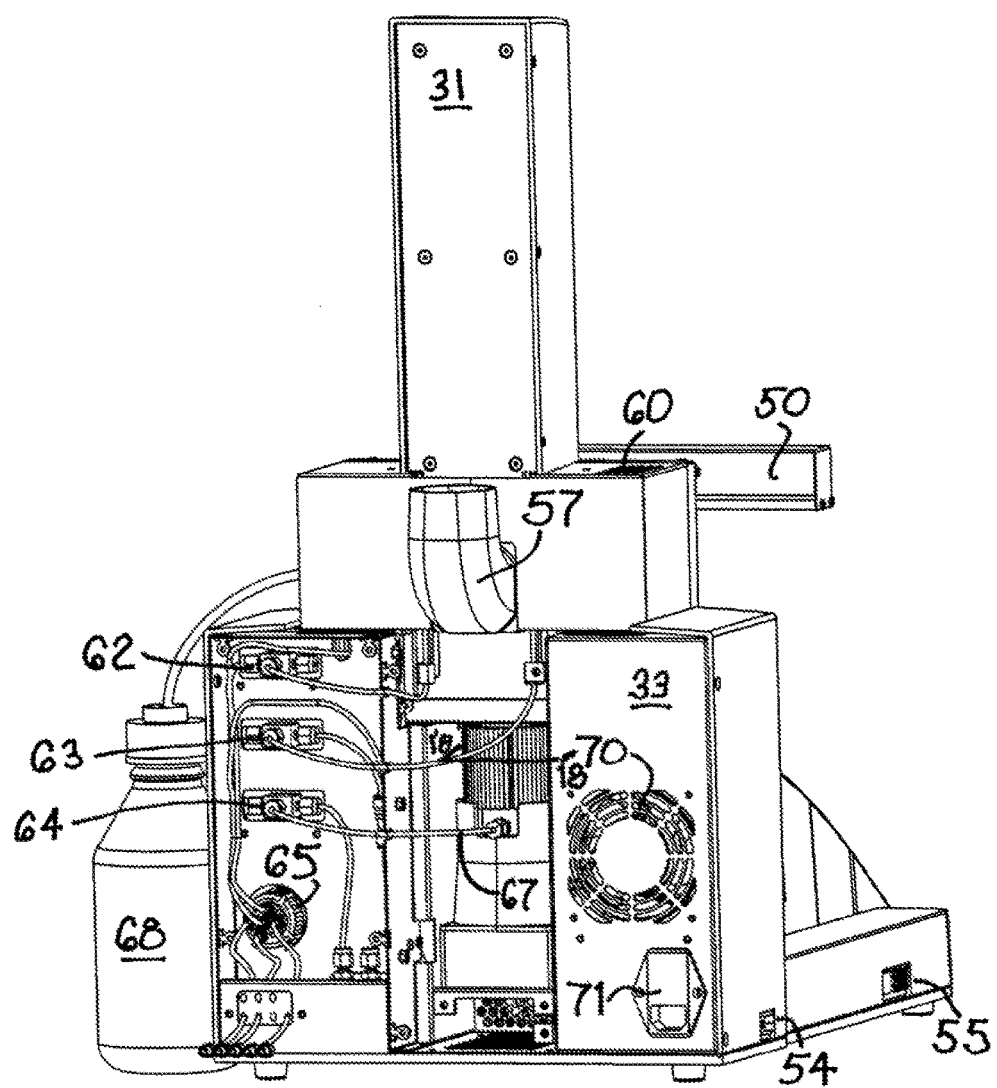
FIG. 3 is a rear perspective view of an instrument according to the invention.

FIG. 3 is a rear perspective view of the instrument 30. An auxiliary valve 62 provides the means for adding liquid samples or other starting materials to a sample cup 45 in the pressure chamber 42. A vent valve 63 allows for the release of gas so that liquids can displace gas in fluid lines and from the pressure chamber 42. The gas agitation valve 64 allows liquid to be released from the chamber, or gas to be bubbled into the pressure chamber 42, or can be closed completely. The auxiliary, vent, and gas valves 62, 63, and 64 are typically ball valves, but it will be understood that other types of valves can be used and that the selection of a small functional valve (and related fluid handling fixtures) for the instrument can be made by the skilled person without undue experimentation.

The multiport valve 65 (e.g., a rotary valve) allows various liquids to be directed as desired. The multiport valve is associated with a plurality of tubes and fittings for the intended purpose, and these likewise can be selected and used without undue experimentation by the skilled person, either in the illustrated arrangement or in other arrangements consistent with the remaining structure and purposes of the instrument 30. For the sake of clarity, not every single possible connection for supplying solvents or removing solvent extracts has been illustrated.

FIG. 3 offers a particularly good view of the heat sink 66 which surrounds the pressure chamber 42. As described herein the instrument 30 heats solvents and sample matrices in the heat resistant pressure chamber 42, but also offers a very convenient rapid return of the solvent to ambient or near-ambient temperature. The heat sink enhances the cooling function.

FIG. 3 also shows a liquid outlet 67 at or near the bottom of the pressure chamber 42 along with associated tubing connecting it to the liquid exit valve 64.

An exhaust vent 70 for helping to cool additional electronics is in portions of the main housing 33. A power supply plug 71 is in lower portions of the main housing 33 and a laboratory bottle 68 is illustrated to show the invention in context (e.g., for supplying solvent or collecting waste).

Figure 4:
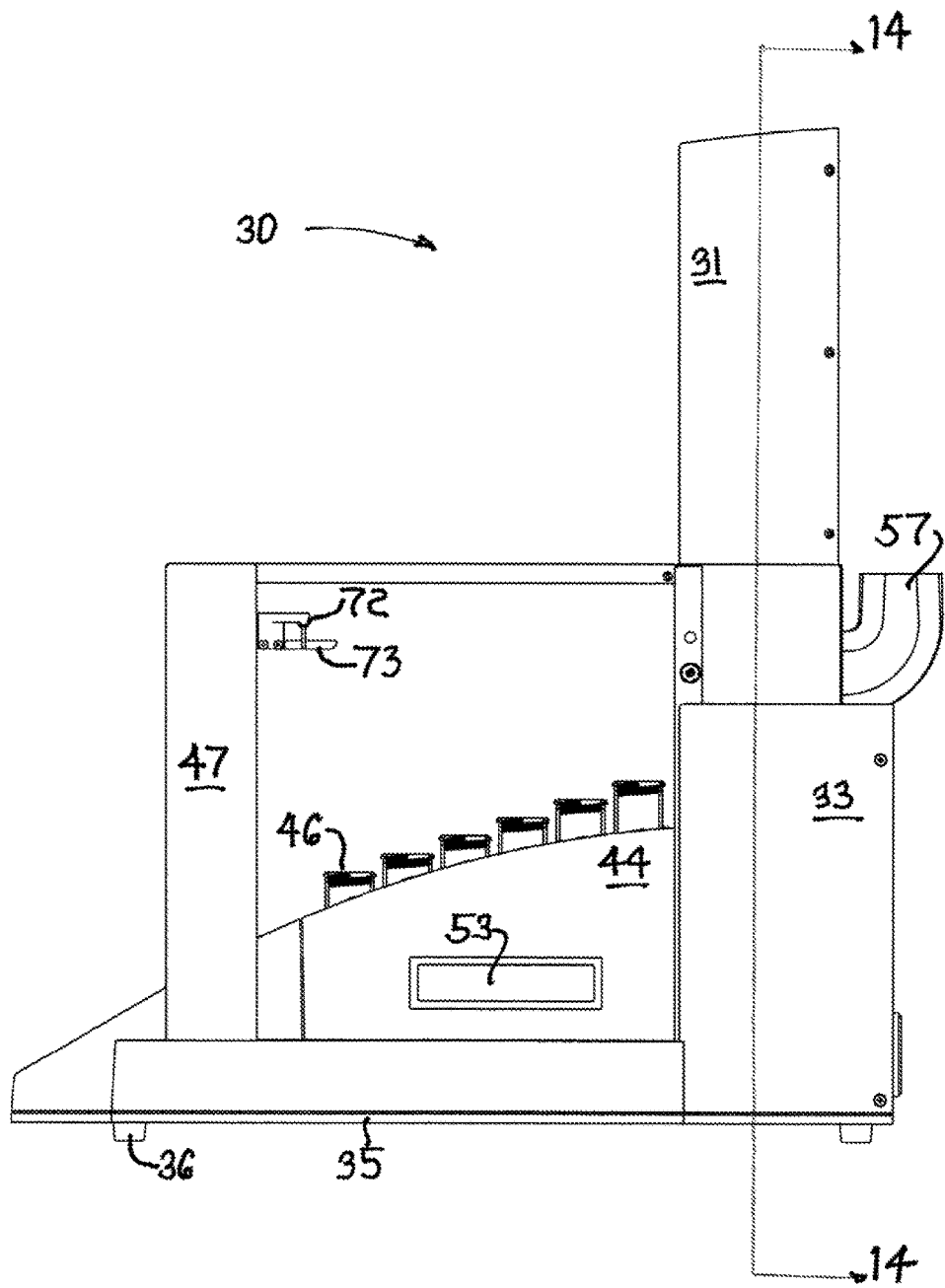
FIG. 4 is a side elevational view of an instrument according to the invention.

FIG. 4 is a side elevational view of the instrument 30. Most of the items in FIG. 4 have been described with respect to FIGS. 1-3, but FIG. 4 additionally illustrates the dispersing faucet 72 and the robot claw 73 on the Y-Z robot, arm 47. As described with respect to FIG. 8, the dispersal faucet 72 is connected (when the desired valves are arranged for this purpose) to deliver solvent extract and analyte from the drain 110 (FIG. 14) to the cooling coil (160 Figure NN) in the chiller 130 (FIG. 10) and then to one of the collection vials 46 after the chamber 42 has been opened to atmospheric pressure. The term "faucet" is used herein in its dictionary sense of a device for controlling the flow of liquid from a pipe with common synonyms including "tap" or "cock."

Figure 5:
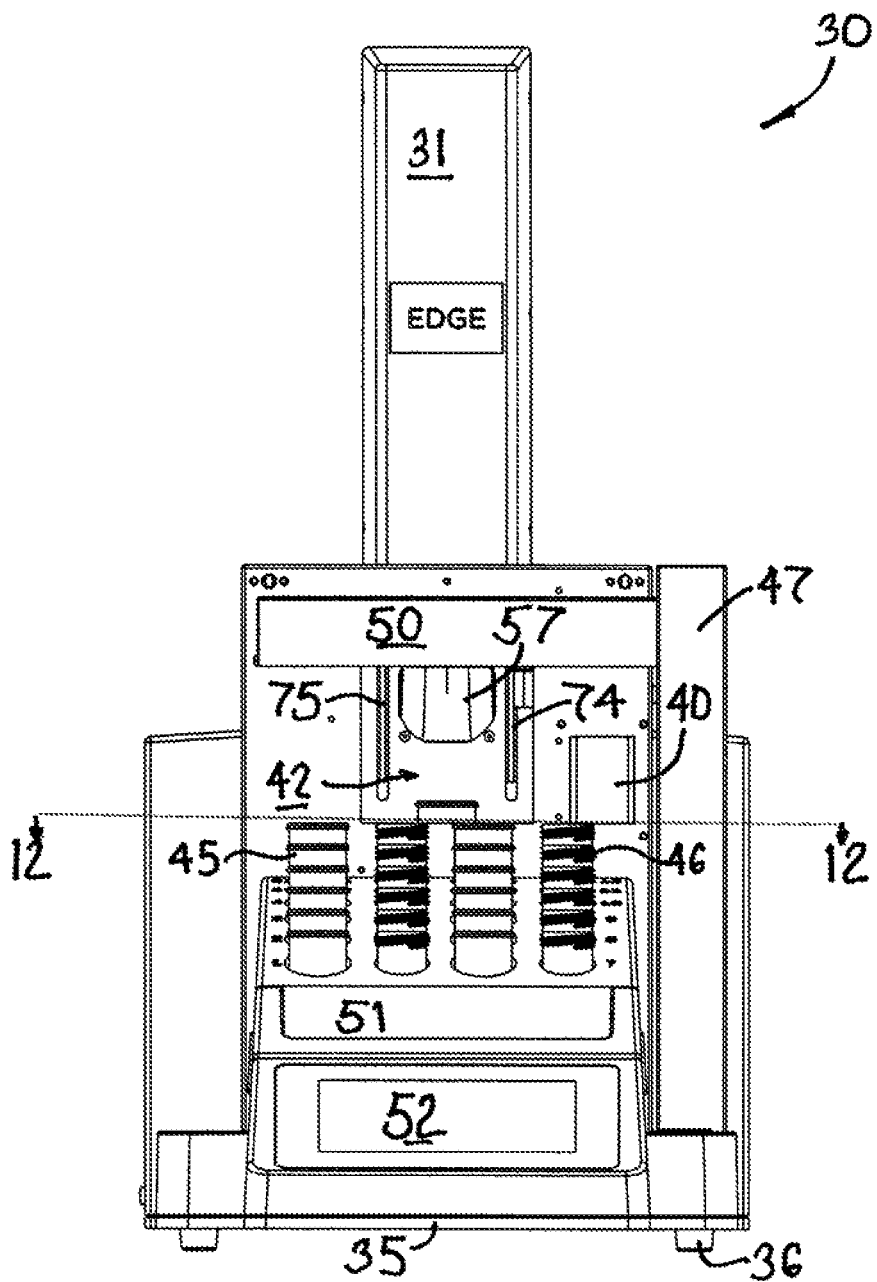
FIG. 5 is a front elevational view of an instrument according to the invention.

FIG. 5 is a front elevational view of the instrument 30 according to the invention. Again. FIG. 5 illustrates items previously described, but adds or clarify some details. In particular FIG. 5 illustrates the parallel slide slots 74 and 75. The slots 74, 75 hold liquid dispensing fixtures in a manner that lets the fixtures move vertically within the chamber housing 32, and are better illustrated in FIG. 6.

FIG. 5 also illustrates that in the illustrated embodiment, the rack 44 holds the sample cups 45 and the collection vials 46 in a riser-like arrangement with the sample cups 45 and the collection vials 46 closest to the chamber housing 30 being highest and those near the spill basin 51 being the lowest.

Figure 6:
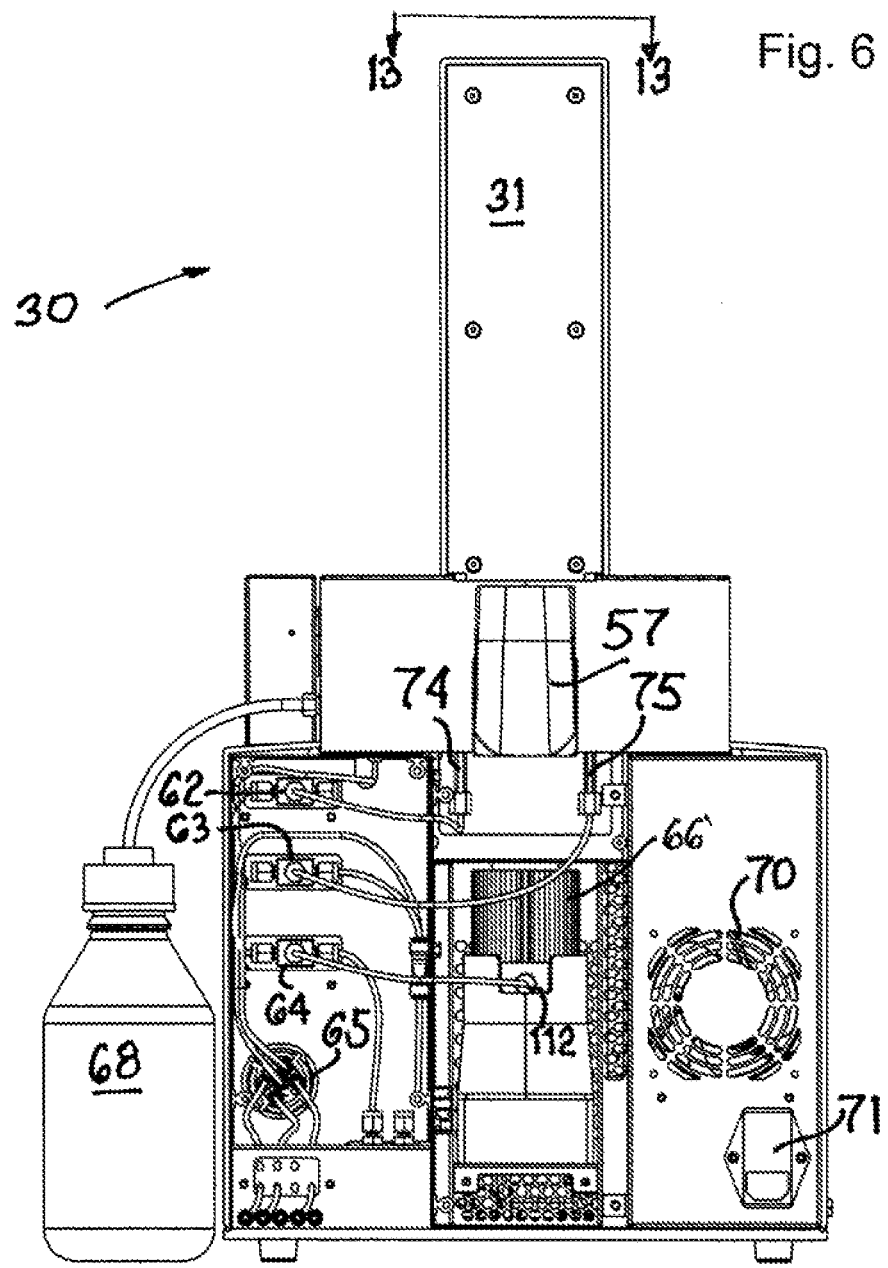
FIG. 6 is a rear elevational view of an instrument according to the invention.

FIG. 6 is a rear elevational view similar to FIG. 3 and with portions of the main housing 33 cover having been removed for purposes of visibility. In particular. FIG. 6 illustrates the slide slots 74, 75 somewhat more clearly along with their slide fittings 76 and 77. The slide fittings 76, 77 in the slots 74, 75 provide a liquid delivery inlet fixture in the thermally conductive pressure resistant heating chamber 42 for delivering liquids (most commonly solvents or rinses) from a supply such as the supply bottle 68 illustrated in both FIG. 3 and FIG. 6.

Figure 7:
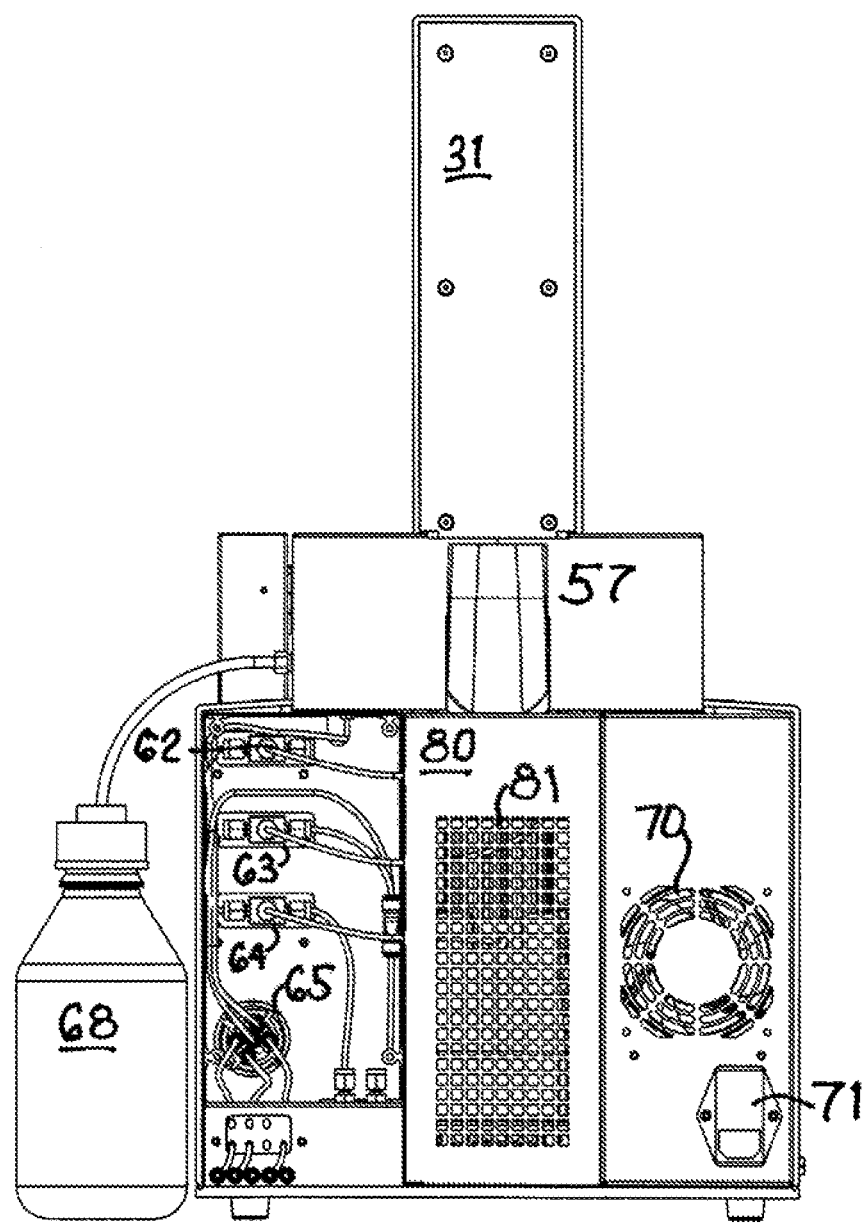
FIG. 7 is a second rear elevational view of an instrument according to the invention.

FIG. 7 is a view identical to FIG. 6 with the exception that FIG. 7 illustrates a rear cover 80 as part of the main housing 33 with the cover 80 carrying a plurality of openings 81 for ventilation and heat transfer (cooling).

In carrying out preparation of a sample for molecular analysis, the sample matrix is placed in the sample cup 45 which is then placed in the thermally conductive chamber 42, following which the closure 43 seals the chamber 42 for press urination. A solvent from a supply (e.g., 68) is delivered to the sample cup 45 (and thus to the sample matrix) through the auxiliary valve 62, the associated tubing (unnumbered), and the delivery head (e.g., 182, FIG. 24). Similarly, a liquid matrix sample can be delivered to the auxiliary valve 62 and thereafter to the chamber 42.

FIG. 8 is a cross-sectional view taken along lines 11-11 of FIG. 2. FIG. 8 illustrates that a lead screw 105 and its motor 106 (both shown generally) cooperate to move the pressure resistant chamber closure 43 over the sample cup 45 in the pressure chamber 42.

The sample cup 45 is positioned in the thermally conductive pressure resistant heating chamber 42 to heat liquids and solids together in the sample cup 45.

Figure 14:
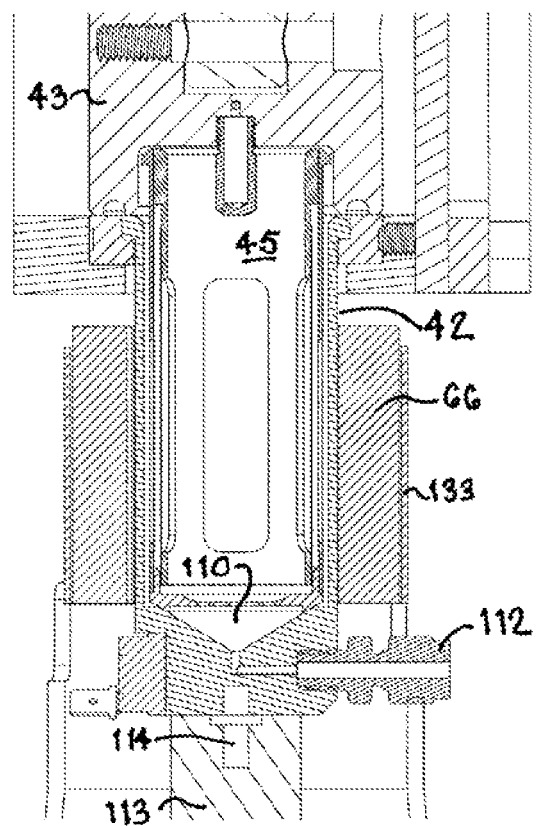
FIG. 14 is an enlarged view of center portions of FIG. 13.

FIG. 8 further illustrates that the sample cup is placed in the pressure chamber 42. In the illustrated embodiment the pressure chamber (shown in more detail in FIG. 14) includes a funnel shaped lower portion 110 into which liquids can drain towards a lateral tube 111 and then a liquid exit port 112 (FIG. 14). When the drained liquid is the extraction solvent containing the analyte, the appropriate valves will direct the solvent extract to the faucet 72 on the X axis robot arm 50 to deliver the extraction solvent and the analyte to one of the collection vials 46.

If additional or secondary agitation of materials in the sample cup 45 is desired or necessary, the ultrasonic generator 113 and its transmitting rod 114 can be incorporated. The ultrasonic generator is typically a piezoelectric generator based upon its combination of size, cost, and reliability, but this is exemplary rather than limiting of this aspect of the invention.

Other details illustrated in FIG. 8 include a cross-sectional view of a row of the sample cups 45, a cooling fan 115, the position of the transparent housing 116, the power supply 117, the control board 120, and the processor 121.

Figure 9:
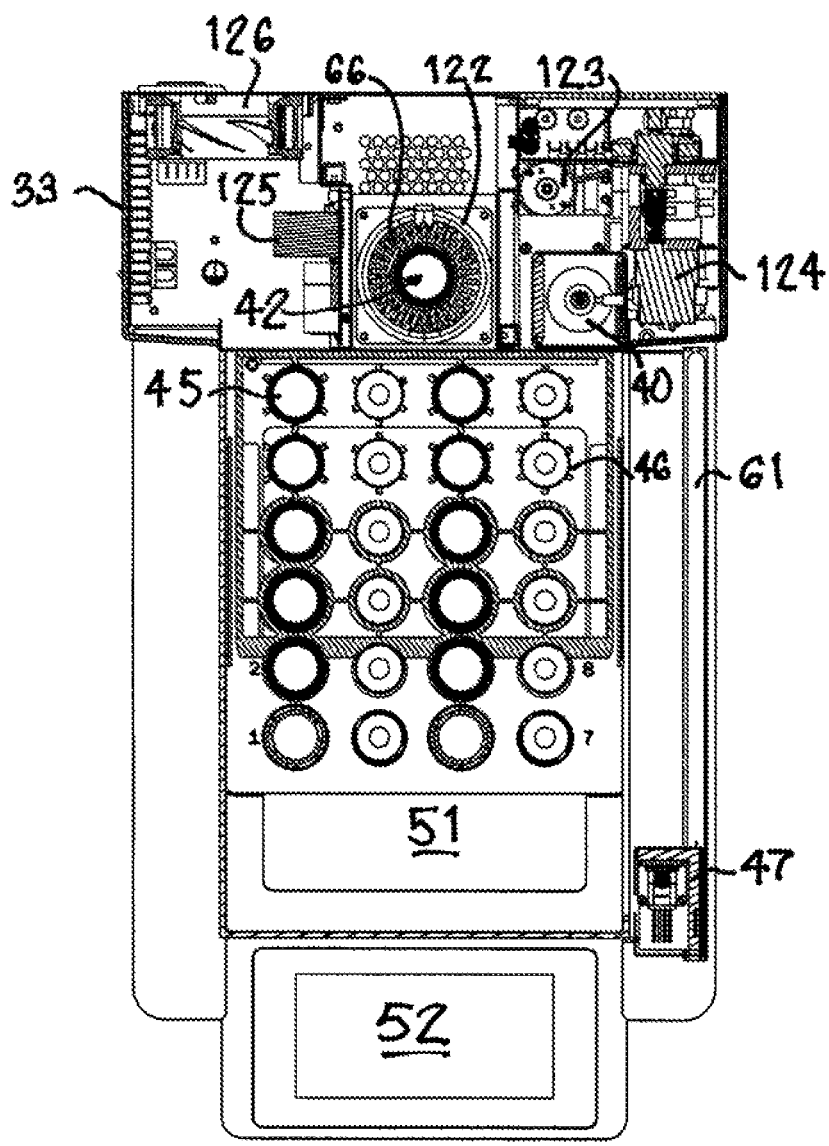
FIG. 9 is a horizontal cross-sectional view taken a long lines 12-12 of FIG. 5.

FIG. 9 is a horizontal cross-sectional view taken along lines 12-12 of FIG. 5, and provides additional details about the invention. A number of elements common to the previous drawings are also illustrated in FIG. 9.

FIG. 9 illustrates that the thermally conductive pressure chamber 42 is in thermal contact with a heater shown as the annular structure 122 separated from the chamber 42 proper by the heat sink 66.

An air pump 123 can purge the pressure chamber as part of the overall exhaust system, and a drive motor 124 for the valves and other mechanical items is illustrated adjacent to the syringe 40. Additional electronics are indicated at 125, and a cooling fan 126 helps maintain a favorable temperature inside the main housing 33, with the vent for the fan having been illustrated in Figure blank.

FIG. 9 also shows the Y-Z robot arm track 61.

Figure 10:
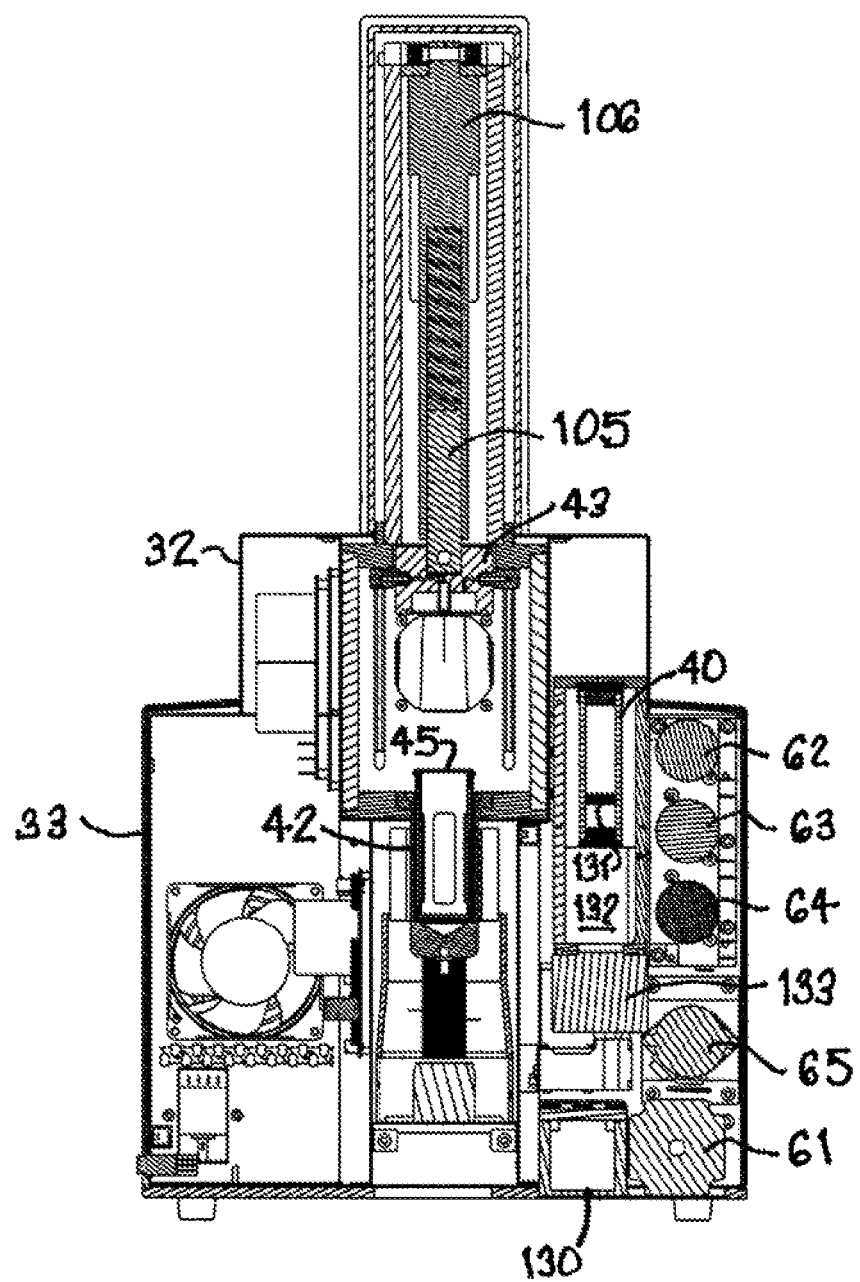
FIG. 10 is a rear cross-sectional view taken along lines 13-13 of FIG. 6.

FIG. 10 is a rear cross sectional view taken along lines 13-13 of FIG. 6 and gives a somewhat different view of a number of the elements already described. FIG. 10 accordingly includes the actuator housing 31, the chamber housing 32, and the main housing 33. The lead screw 105 and the lead screw motor 106 are illustrated with the chamber top 43 in the open position above the chamber 42 and the sample cup 45.

In comparison to previous drawings, FIG. 10 most helpfully illustrates the chiller shown in the form of the coil housing 13. The coil 160 is in liquid communication with the sample cup 45 in the pressure resistant heating chamber 42 and receives heated liquids from the pressure resistant heating chamber 42 when the chamber 42 is opened to atmospheric pressure. The coil in the coil housing 130 has a length sufficient to reduce the temperature of common extraction solvents to useful handling temperatures with a range of from between about 50° C. and 180° C. to between about 25° C. and 40° C. being exemplary (but not limiting) as the solvent travels the length of the cooling coil.

FIG. 10 also illustrates the syringe 40, the syringe piston 131, the syringe drive 132, and the syringe drive motor 133. FIG. 10 includes cross-sectional views of a number of elements previously described including the auxiliary valve 62, the vent valve 63, the gas valve 64, the multiport valve 65, and the Y-Z axis robot track 61.

Figure 11:
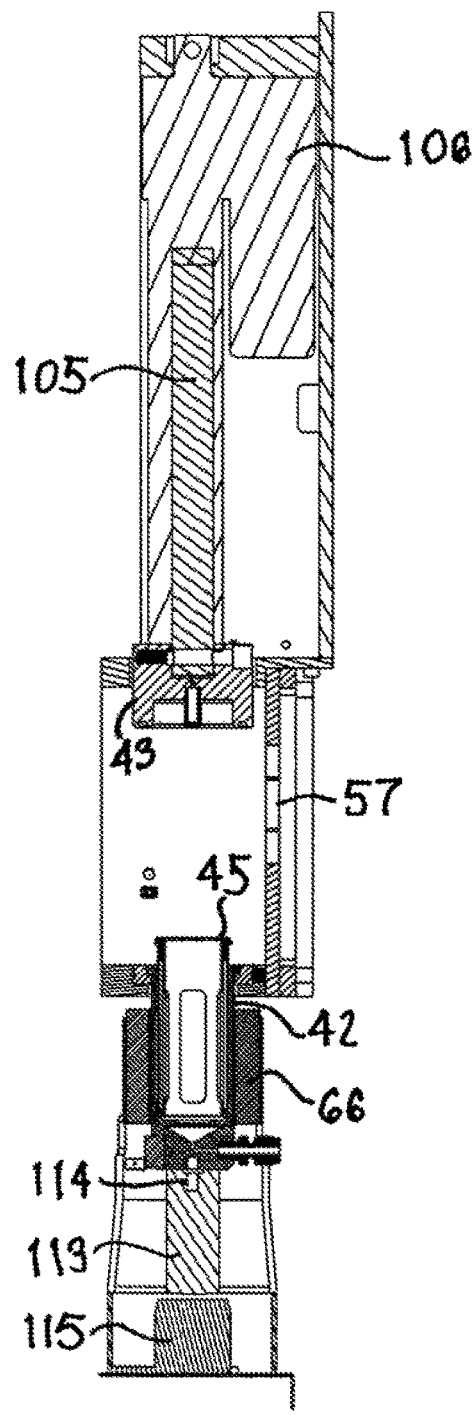
FIG. 11 is an isolated cross-sectional view taken along lines 11-14 of FIG. 4.
Figure 12:
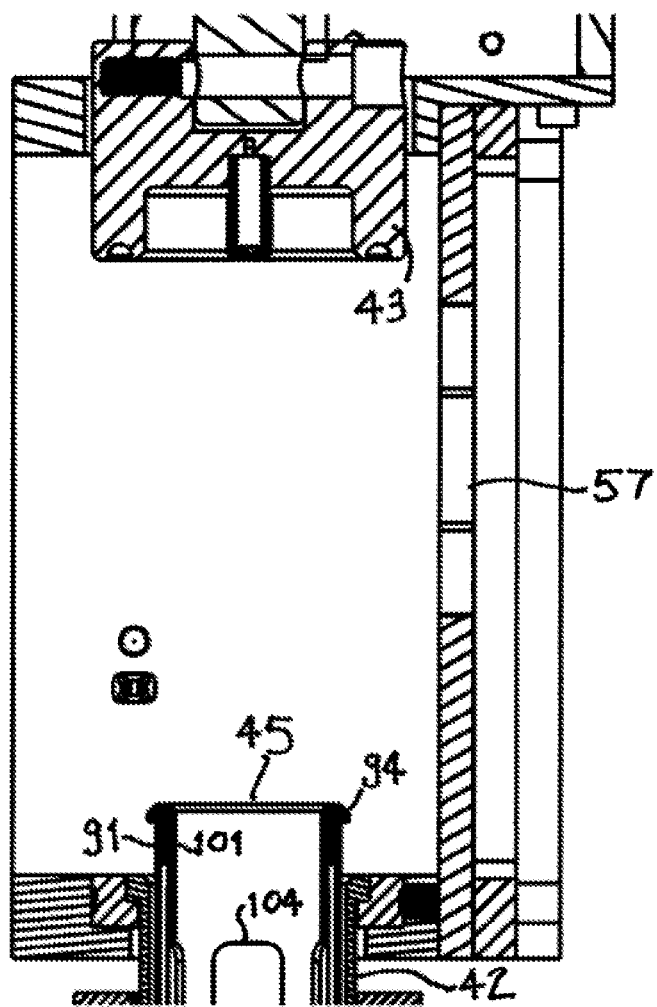
FIG. 12 is an enlarged portion of FIG. 11.
Figure 15:
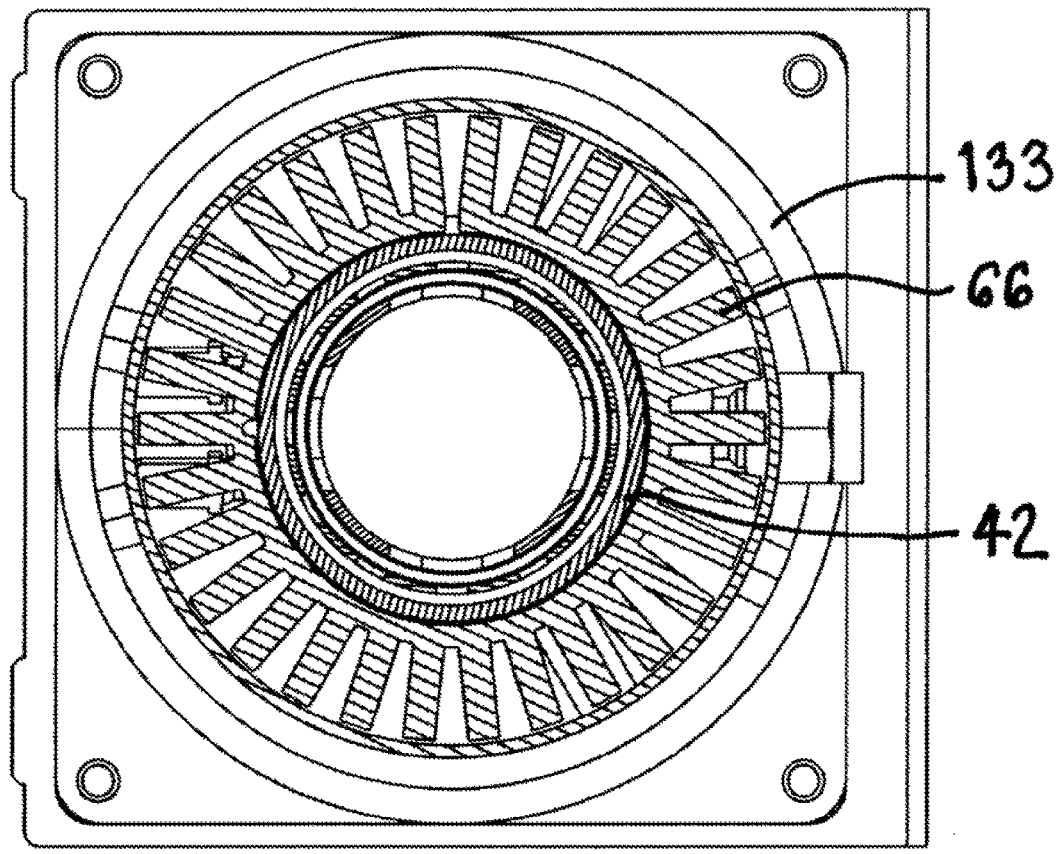
FIG. 15 is a cross-sectional view taken along lines 18-18 of FIG. 3.

FIG. 11 represents an isolated cross-sectional view taken along lines 14-14 of FIG. 4 and illustrating center portions of the instrument 30 illustrating many of the same elements as previously described, and FIG. 12 represents an enlarged portion providing somewhat greater detail. FIGS. 14 and 15 illustrate the chamber 42 and chamber closure 43 in the opened position.

Figure 13:
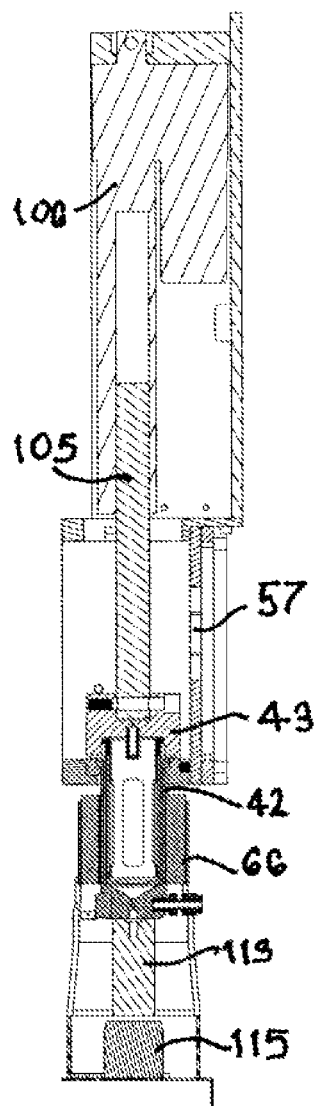
FIG. 13 is analogous to FIG. 11, but with the pressure chamber closed.

FIG. 13 is analogous to FIG. 11, but showing the lead screw 105 having moved to place the chamber closure (chamber top) 43 on the remainder of the chamber 42 to illustrate the position in which the extractions and related procedures are carried out.

FIG. 14 is an enlarged view of center portions of FIG. 13.

FIG. 15 is a cross sectional view taken on a horizontal plane of the sample cup 45 positioned in the pressure resistant heating chamber 42, surrounded by the heat sink 66 which in turn is surrounded by the heater 133. Because the heat sink is favorably thermally conductive, it efficiently transmits heat to and from the chamber 42 and thus to and from the contents of the sample cup 45.

Use and Experimental

In an exemplary use of the instrument 30, an extraction solvent and a sample matrix are placed into the sample cup 45, and the sample cup 45 is positioned in the pressure resistant heating chamber 42. Typical (but not limiting) sample matrices include food, food packaging, and soil.

As recognized by the skilled person (e.g., US EPA Method 3545) samples should be extracted using a solvent system that gives optimum reproducible recovery of the analytes of interest from the sample matrix, at the concentrations of interest. The choice of extraction solvent depends on the analytes of interest and no single solvent is universally applicable to all analytes.

Typical (but not limiting) solid-liquid extraction solvents for molecular analysis include water, weak acids, weak bases, acetone, hexane 2-propanol, cyclohexane, dichloromethane, acetonitrile, methanol, and mixtures thereof.

Common solvents used for liquid/liquid extraction are water, weak acids, weak bases, ethyl acetate, methyl tertiary-butyl ether ("MTBE"), dichloromethane ("methylene chloride"), hexane, and mixtures thereof.

The extraction solvent and the sample matrix are mixed in the sample cup 45 in the chamber 42. An advantage of the instrument is the capacity to carry out extraction on loose—as opposed to tightly packed—samples. Although the term "loose" is relative, it is used here in its normal sense as being free from anything that binds or restrains and free or released from fastening or attachment (Urdang, THE RANDOM HOUSE COLLEGE DICTIONARY, Random House Inc. (1972)). Because the sample matrix is loose, the addition of solvent from the top, the bottom, or both, helps disperse the sample matrix in the solvent.

The instrument, can also be used to encourage the sample to disperse in the solvent by applying a thermal gradient; using an agitating flow of a gas that is otherwise inert to the sample matrix, the analyte or the solvent; or in some applications ultrasonic vibration. Those skilled in the extraction art will recognize that an agitating gas can be selected based on known parameters, and that in some cases compressed air will be appropriate while in others nitrogen, one of the noble gases (e.g., helium, argon), or hydrogen may be best (with care based upon hydrogen's flammable characteristics).

Other mixing techniques can be used (e.g., magnetic stirrers or other mechanical devices), but will require more complex instrumentation.

The sample matrix and the solvent are then heated in the sample cup 45 in the chamber 42 to a temperature at which evaporated solvent generates an above-atmospheric pressure. A temperature of 50° C.-180° C. is exemplary (the US Environmental Protection Agency suggests 120° C. for soil), at which temperature typical organic extraction solvents generate a corresponding pressure of 50-250 pounds per square inch (psi). In experiments to date, the time to reach this temperature is about 90 seconds, at which point extraction is substantially complete (it being understood that extraction is an equilibrium process). The pressure generated by the vapor from the solvent is then used to drain the solvent extract from the sample cup into the cooling coil (160, FIG. 24) in chiller 130 that has a length sufficient to reduce the temperature of the extract to near ambient (e.g., 25° C.) while the solvent extract is in the coil. The solvent extract is then collected from the coil 160, typically in a collection vessel 46. In exemplary experiments, metal tubing with a length of about 10 feet tends provide a dwell time of about 30 seconds, which is sufficient to cool the solvent extract to ambient or near-ambient temperature. Thus, the coil is typically used for space saving purposes, but a coil shape is optional rather than mandatory.

The sample matrix and the extraction solvent can be added in amounts that are typical in this Held. For example, a solid matrix is collected in a manner that provides between about 5 or 10 grams (g) of the sample matrix of interest. The amount of extraction solvent, will be proportional; typically about 30-100 milliliters (mL).

The draining step takes place when the auxiliary valve 62 is opened to atmospheric pressure so that the pressurized solvent vapor in the thermally conductive chamber 42 pushes the liquid solvent extract out through the port fitting 112 and then to the cooling coil 160.

The instrument 30 is also useful for extraction based sample preparation that includes the step of placing a solvent, adsorbent particles, and a sample matrix that contains an analyte into the sample cup 45, with the improvement steps of heating the vessel, the sample matrix, the adsorbent particles and the solvent in the pressure resistant chamber 42 until the temperature generates an above atmospheric pressure that together with the increased temperature drives the analyte substantially from the sample matrix into the solvent.

In this aspect, the instrument 30 according to the invention provides a faster and simpler alternative to both SPE and dispersive SPE. The absorbent particles can be those typically used for the stationary phase in such methods.

In particular, the selection of adsorbent particles can be based on factors that are well known in the art, and for the most part upon the polarity of the extraction solvent and the polarity of the expected analyte. In general molecules of similar polarity attract one another and this factor is used in a number of separation based fields of analysis and sample preparation including liquid or gas chromatography, solid phase extraction, dispersive solid phase extraction, and the present invention.

Generally, salts are considered the most highly polar followed closely by acids, and then the smaller alcohols. Fluorinated organic compounds are the least polar, followed closely by aliphatic and aromatic compounds.

Solvents within each of these categories are similarly well understood. Similarly, the characteristics stationary phases such as silica are well understood. In particular, unbonded silica tends to be hydrophilic (polar), but can be modified by adding various functional groups to change the characteristics towards lower polarity; e.g., Arsenault 2012, supra, at page 138.

Obviously, a wide ranging selection is available to the skilled person, and because the instrument 30 uses the same solvents and stationary phases as other methods, appropriate choices can be made without undue experimentation.

In another aspect, the instrument 30 can also prepare liquid matrices that include the analyte of interest. In this aspect, the method includes the steps of adding a liquid sample matrix to a plurality of particles that carry an extraction solvent. Such particles are also referred to as solvent impregnated resins ("SIRs"). The solvent carrying particles are positioned in the sample cup. The particles and the liquid matrix are agitated, heated, and pressurized in the sample cup to extract the analyte from the heated liquid sample matrix and into the Solvent carried by the particles.

Thereafter the pressurized heated liquid matrix is drained by opening the chamber 42 to atmospheric pressure and this liquid leaves the sample cup through the foraminous floor 147.

In the next step, a release solvent is added to the porous particles carrying the extraction solvent and the analyte. The agitating, heating and pressurizing steps are repeated for the release solvent and the particles to release the analyte into the release solvent. The release solvent is then drained by opening the thermally conductive chamber 42 to atmospheric pressure to allow the release solvent to travel in the cooling coil 160 until the drained release solvent reaches ambient or near-ambient temperature, after which it is collected for analysis.

Appropriate particles are generally well understood in the art and are typically formed of a physically durable water insoluble polymer resin in a mesh size (or range of mesh sizes) that will be retained by the porous sleeve, and typically with a broad distribution in pore sizes. The polymer should, of course, remain stable at the temperatures and pressures generated in the extraction steps.

Typical particles are formed from resins such as hydrophobic cross-linked polystyrene copolymer resins: polymers based on styrene cross-linked with divinyl benzene, and polymerized methacrylic acid ester. See, e.g., Kabay et al, *Solvent-impregnated resins (SIRs)—Methods of preparation and their applications*; Reactive & Functional Polymers 70 (2010) 484-496.

As in the previous embodiments, the step of draining the release solvent includes draining the healed release solvent to the cooling coil 160 in the manner previously described. At that point, the release solvent containing the analyte is at a temperature ready for molecular analysis in conventional equipment.

Basically, the instrument 30 can be used to prepare any analyte that is stable at the expected temperatures and pressures.

Some examples of analytes for which the methods described herein are suitable include aromatic and aliphatic compounds such as: benzene, toluene, ethyl benzene, xylene(s), cumene, limonene, nitrobenzene, cresol(s), higher alkylated phenols, octanol, nonanol, decanol, hexane, heptane, methyl isobutyl ketone (MIBK), tetrahydrotiophene, cs2, tetramethyltetrahydrofuran, and methyl tert-butyl ether (MTBE), among others.

The instrument 30 can also prepare samples containing halogenated/chlorinated compounds such as monochloromethane, dichloromehane, trichloromethane, tetrachloromethane, dichloroethane (1,1 & 1,2), trichloroethane, tetrachloroethane,chloroethylene, dichloroethylene, trichloroethylene,tetrachloroethylene, trichloropropane, chlorobutadiene, hexachlorobutadiene, monochlorobenzene, dichlorobenzen, chlorobenzenes, chloroaphtalene, hexachlorocyclohexane, monochlorophenol, dichlorophenol, trichlorophenol, dichloro-di-isopropylether, and dioxins.

The instrument 30 can also prepare samples containing polyaromatic hydrocarbons such as PCBs, naphtalene, acenaphtylene, acenaphthene, flourene, phenanthrene, anthracene, flouranthene, pyrene, benz(a) antharacene, chrysene, and dibenzothiophene.

Solvents can be selected from the group consisting of water, weak adds, weak bases, ethyl acetate, methyl tertiary-butyl ether ("MTBE") methylene chloride, hexane, acetone, hexane 2-propanol, cyclohexane, acetonitrile, methanol and mixtures thereof, but are not limited to that particular group.

The instrument 30 can also be used for techniques that add adsorbent particles to the sample cup with the solid matrix and the extraction solvent. The use of an appropriate extraction solvent and resin particles will transfer the analyte from the solid matrix to the resin particles, following which the extraction solvent can be drained to waste, and a release solvent added to the mixture of solid matrix and adsorbent particles to release the analyte into the release solvent. The remaining steps are the same.

Experimental

TABLE 1

Example 1
Environnmental Application: Extraction or BNA's from soil

| Method | Sample Size (g) | Solvent (1:1 v/v) | Volume (mL) | Time (minutes) | Temperature (° C.) | Pressure (psi) |
|---|---|---|---|---|---|---|
| Soxhlet | 10 | Hexane/Acetone | 150 | 1440 | 100 | N/A |
| Example 1 | 5 | Hexane/Acetone | 30 | 5 | 100 | <350 |
| ASE | 5 | Dichloromethane/Acetone | 50 | 26 | 100 | 1500 |

Table 1 plots data from the extraction of bases neutrals and acids ("BNA's") from soil comparing Soxhlet (EPA 3540C), the current invention (Example 1), and accelerated solvent extraction (ASE; EPA 3545). The volume and time for the indicated ASE's are taken from a run using the parameters set forth in Dionex application note 317. Analysis was carried out using gas chromatography followed by mass spectroscopy (GCMS: EPA 8270).

The instrument 30 uses significantly less solvent and takes significantly less time than the other methods. In particular, the preparation of the ASE extraction cell is generally tedious with over 10 components and steps, whereas the instrument 30 uses just three straightforward pieces (the sleeve 80 and its supports 87 and 90). On average, preparation of an ASE extraction cell takes about 15 minutes, while the invention is ready in a few seconds.

TABLE 2

Environmental Application, Extracton of BNA's from soil; CRM Recovery Data (%)

| Analyte | Proficiency |
|---|---|
| Phenol | 60.0 |
| Hexachloroethane | 51.1 |

| Analyte | Soxhlet | % Proficiency Soxhtet |
|---|---|---|
| Phenol | 48.9 | 81.5 |
| Hexachloroethane | 38.6 | 75.5 |

| Analyte | ASE | % Proficiency ASE |
|---|---|---|
| Phenol | N/A | N/A |
| Hexachloroethane | 32.2 | 63 |

TABLE 2-continued

Environmental Application, Extracton of BNA's from soil; CRM Recovery Data (%)

| Analyte | Invention | % Proficiency Invention |
|---|---|---|
| Phenol | 60.2 | 100 |
| Hexachloroethane | 45.6 | 89.2 |

Table 2 summarizes the data by percentage for BNA's in certified reference material (CRM) soil obtained from Waters Corporation (Milford, Mass. 01757 U.S.A.; ERA catalog number 727). As understood by those in the art, the goal is to obtain 100% recovery of the materials known to be present in the CRM sample. For each method, all of the recoveries were within the quality control performance acceptance limits, but the invention (Example 1) recovered all 39 analytes, while ASK recovered only 38, and failed to identify 2-methylnaphthalone. The invention accordingly had the best overall performance in terms of the analytes recovered and the percent recovery of the analytes.

Figure 16:
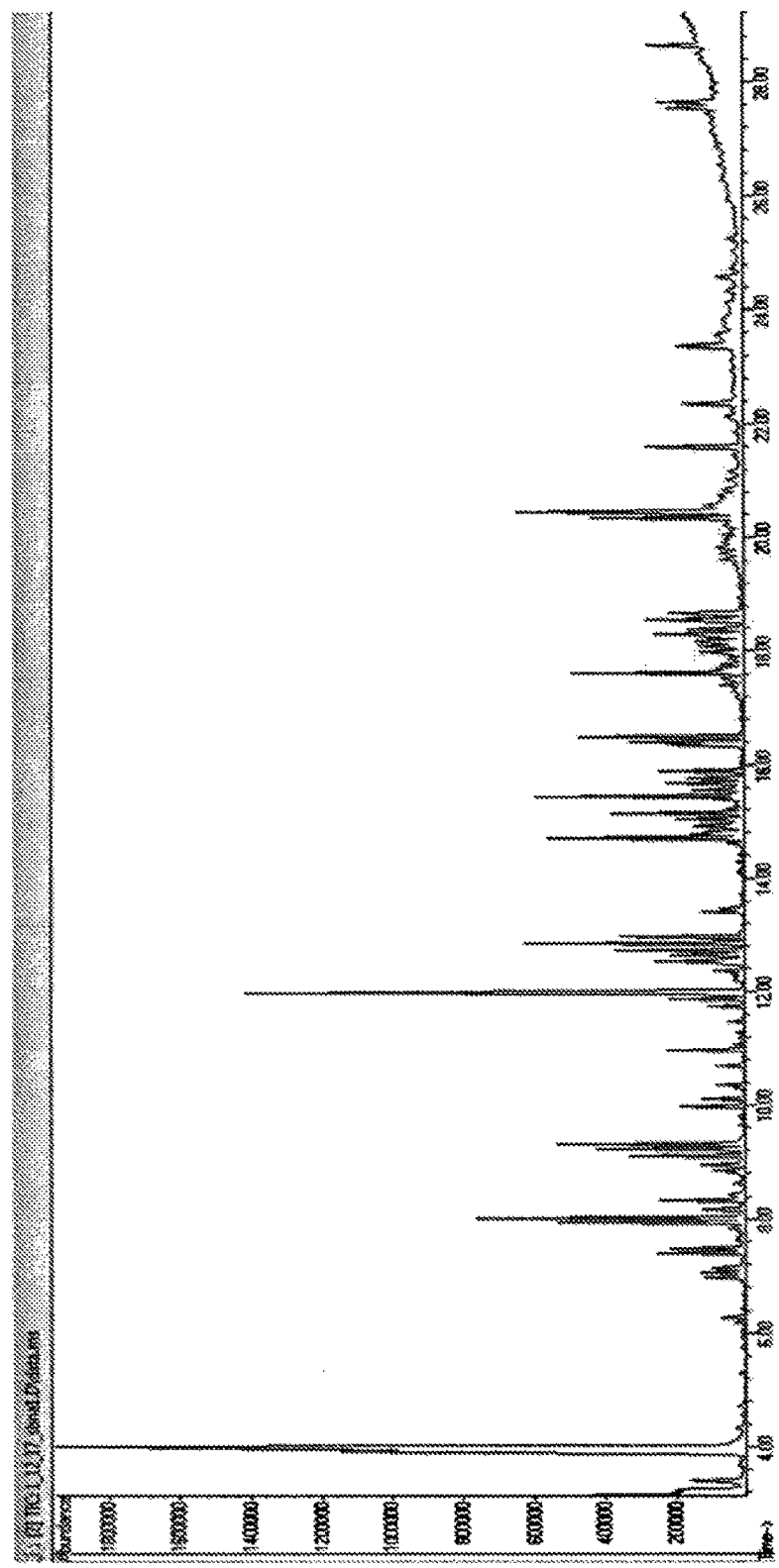
FIG. 16 is an exemplary full scan chromatogram of experimental results using the instrument of the invention.

FIG. 16 is an exemplary full scan chromatogram of the BNA CMR extraction based on Example 1.

Figure 17:
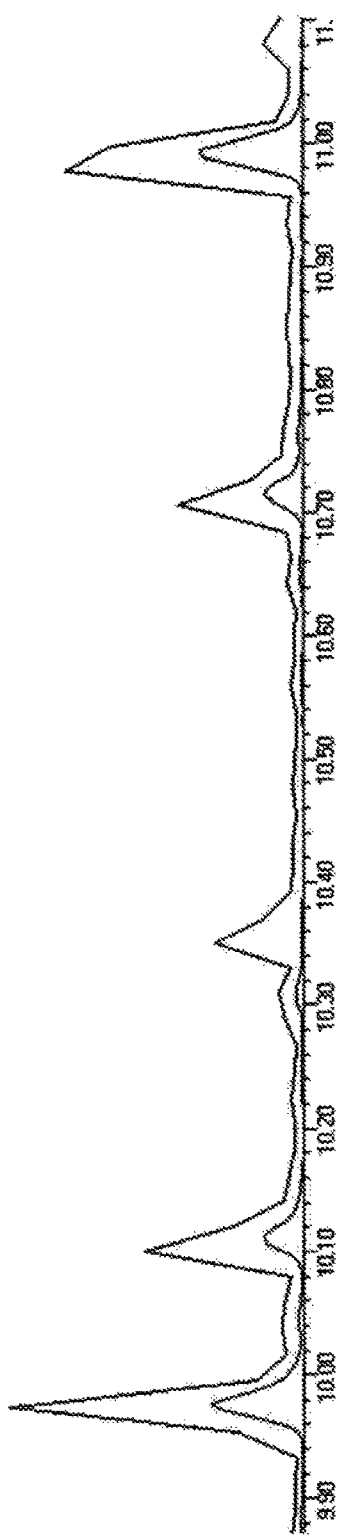
FIG. 17 is an overlay according to the invention as compared to ASE extraction.

FIG. 17 is an overlay of the Example 1 extraction carried out in the instrument 30 as compared to the ASE extraction. Each of the higher peaks represents the Example 1 extraction which outperformed ASE in recovery. Additionally, the absence of an ASE peak at retention time 10.36 (2-methylnaphthalene) demonstrated the failure of ASE to identify this analyte.

TABLE 3

Example 2
Extraction of Phthalates from Polyethylene

| Method | Sample Size (g) | Solvent (70:30 v/v) | Volume (mL) | Time (minutes) | Temperature ° C. | Pressure (psi) |
|---|---|---|---|---|---|---|
| Soxhlet | 0.5 | Acetone/Cyclohexane | 150 | 1440 | 100 | N/A |
| Example 2 | 0.5 | Acetone/Cylcohexane | 30 | 10 | 140 | <350 |
| ASE | 0.5 | Hexane | 50 | 63 | 120 | 1500 |

Table 3 is a comparison chart as between Soxhlet, the instrument 30 (Example 2), and ASE for the extraction of phthalates from polyethylene. The volume and time for ASE are from a run using the parameters stated in a Dionex publication (Knowles, D; Dorich, B; Carlson, R; Murphy, B; Francis, E; Peterson, J, Richter, B. "Extraction of Phthalates from Solid Liquid Matrices," Dionex Corporation, 2011) and all methods were based oft of CPSC-CH-C1001-09.1 (Consumer Products Safety Commission, Test Method: CPSC-CH-C1001-09.3 Standard Operating Procedure for Determination of Phthalates; http://www.cpsc.gov/about/cpsia/ CPSC-CH-C1001-09.3.pdf).

Again, the instrument 30 (Example 2) used significantly less solvent and took significantly less time than the other methods.

TABLE 4

Example 2
CRM Recovery Data (%)

| Analyte | Soxhlet | Example 2 | % Soxhlet Example 2 | Example 2 w/ Agitation* | % Soxhlet Example 2 w/ Agitation* | ASE | % Soxhlet ASE |
|---|---|---|---|---|---|---|---|
| Bis (2-ethylhexyl) phthalate | 72.6 | 57.7 | 79 | 73.4 | 101 | 24.3 | 33 |
| Di-n-octyl phthalate | 85.5 | 68.2 | 80 | 80.7 | 94 | 31.4 | 37 |

Table 4 compares the recovery data by percentage for extraction of phthalates from polyethylene in a CRM sample (SPEX CertiPrep CRM-PE001; Metuchen, N.J. 08840, USA). In this experiment agitation was carried out with 30 seconds of both bubbling and sonication prior to heating. Again, the instrument 30 (Example 2) recovery data was significantly better than ASE and showed an improvement with the use of agitation. Example 2's results with agitation match Soxhlet data which is considered the "gold standard" for extraction. All analytes in the CRM were recovered for all methods.

Figure 18:
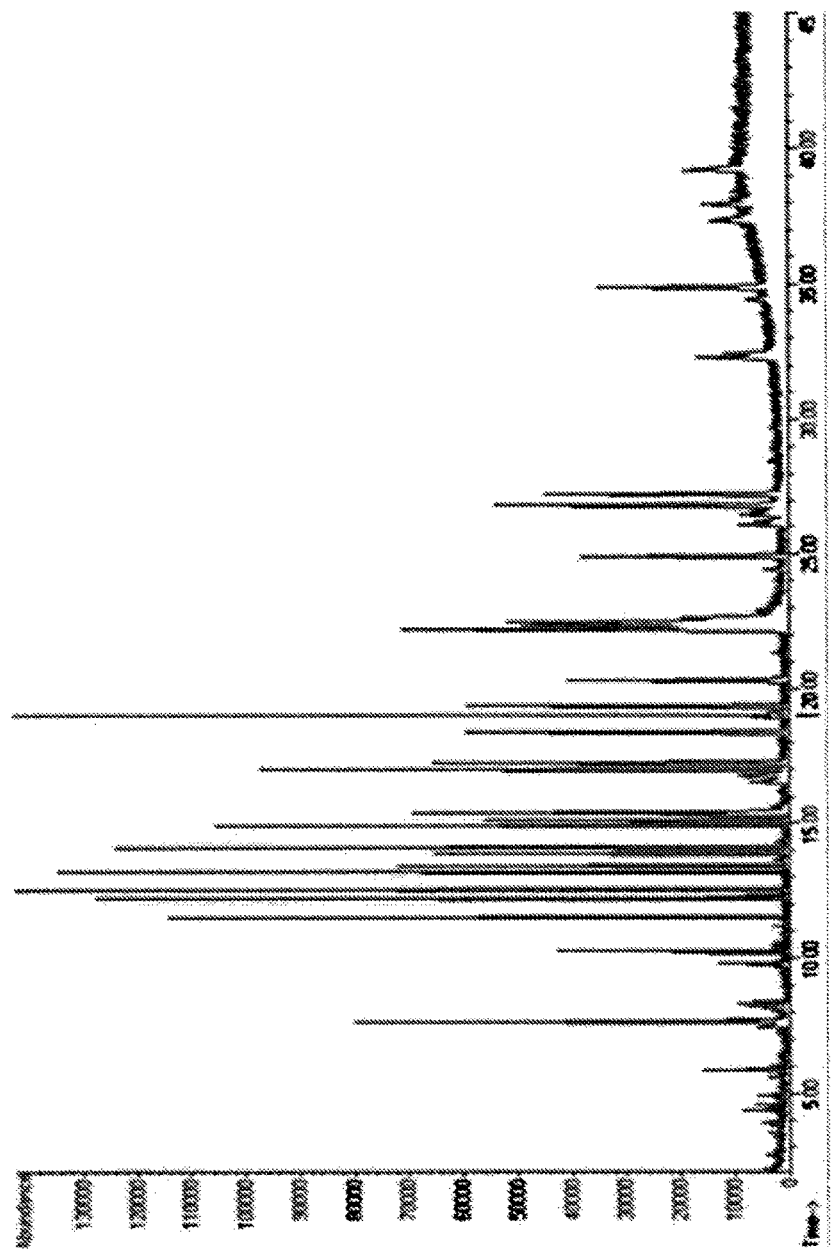
FIG. 18 is a sample full scale chromatogram of another experiment carried out using the instrument according to the invention.

FIG. 18 is a sample full scan chromatogram of the Example 2 polyethylene CRM extraction using the instrument 30.

Example 3—Extraction of Pesticides from Soybeans

In another aspect, the invention provides an improvement upon the dispersive SPE ("dSPE") method referred to in the art as QuEChERS. QuEChERS is an accepted extraction and matrix clean up procedure for multi-residue analytes in a variety of different matrices. The invention is an alternative option to QuEChERS that offers comparable results easily, quickly and reliably

| Method | Time (min) | Automated |
|---|---|---|
| Invention | 5 | Yes |
| QuEChERS | 20 | No |

The invention is both faster than QuEChERS and automated, creating a more efficient lab.

Example 3 compared the invention against the AOAC 2007.01 9 (QuEChERS) Procedure, which includes the following steps:

Sample Extraction

1. Transfer 10-15 g of homogenized sample to 50 mL centrifuge tube;
2. Per 15 g sample, add 15 mL 1% acetic acid in acetonitrile plus contents of acetate tube
3. Shake vigorously for 1 min.
4. Centrifuge at above 1500 U/min for 1 min.

Sample Cleanup

1. Transfer 1 mL of acetonitrile layer to a dSPE 2 mL tube;
2. Shake vigorously for 1 min;
3. Centrifuge at above 1500 U/min for 1 min;
4. Transfer the supernatant to a GC vial for concurrent GCMS analysis.

The entire process takes around 20 minutes of constant manual work.

Example 3: In the invention, sample extraction and sample clean up are carried out together:

1. Transfer the homogenized food sample to the sample cup and add dSPE sorbent;
2. Place the sample cup in the heated pressure resistant chamber;
3. Heat the sample cup in the pressure resistant chamber for 5 minutes;
4. Transfer the extract to a GC vial for concurrent GC-MS analysis.

The entire process takes only 5 min per sample and is automated.

TABLE 5

Example 3

| Pesticide | Method | Recovery (%) |
|---|---|---|
| Cyprodinil | Example 3 | 90 |
| Cyprodinil | QuEChER S | 95 |
| Cyprodinil | QuEChERS | 85 |
| Chlorpyrifos | Example 3 | 125 |
| Chlorpyrifos | QuEChERS | 98 |

Figure 19:
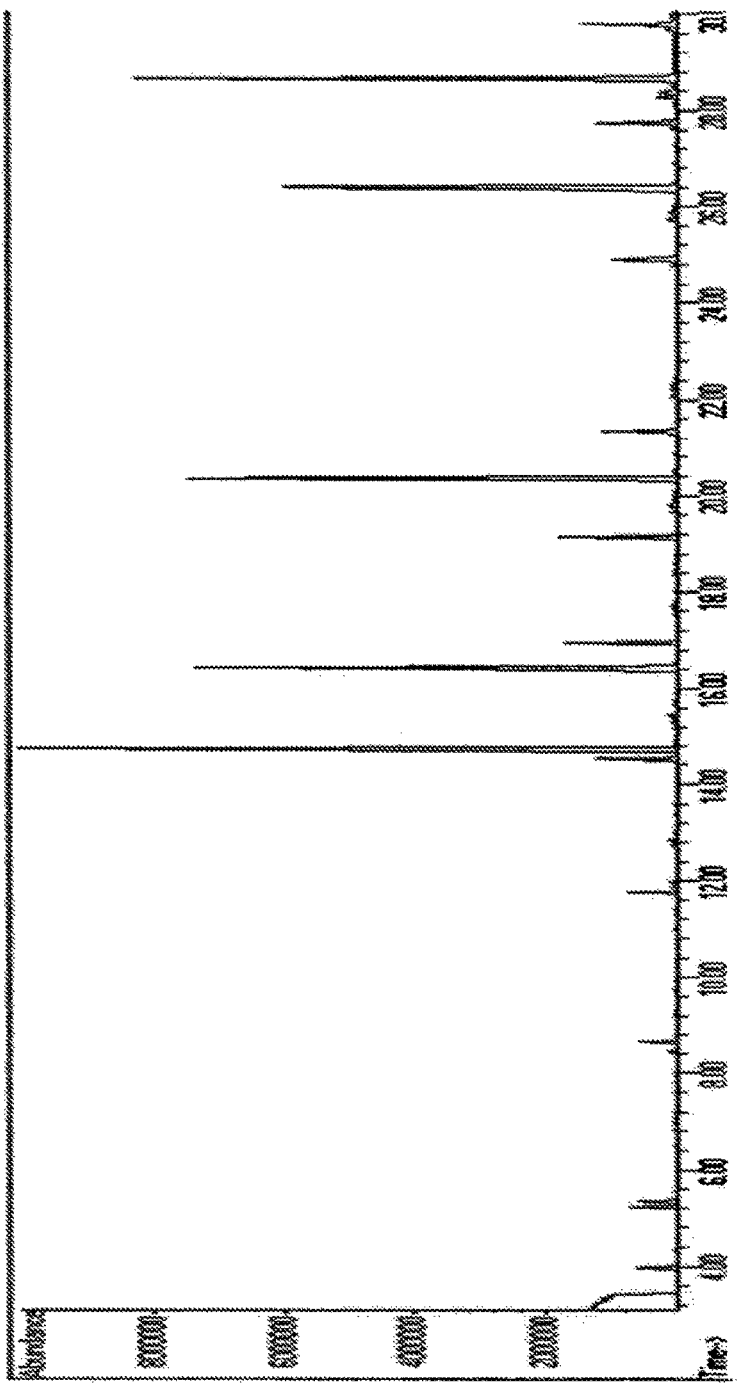
FIG. 19 is a full scan chromatogram of another experiment carried out according to the invention.

Table 5 is a comparison of the invention's Example 3 results to the QuEChERS results for the extraction of pesticides from soybeans. The QuEChERS data is based on published recoveries for AOAC method 2001.01 (Journal of Chromatography A. 1271 (2010) 2548-2560). The invention (Example 3) achieved comparable results to those published. In comparison, QuEChERS data can vary widely due to the manual nature of the procedure FIG. 19 is a full scan chromatogram of the results of the Example 3 soybean extraction carried out using the method of the invention.

FIGS. 20-23 illustrate an embodiment that has particular advantages when the vapor pressure of the heated solvent may not be sufficient to move the extraction solvent from the thermally conductive reaction chamber efficiently or completely Based upon certain differences from the previously illustrated embodiments, some of the elements in FIGS. 20-23 may be named and numbered differently than similar (but not necessarily identical) parts previously described. FIG. 24 is a schematic diagram.

Figure 20:
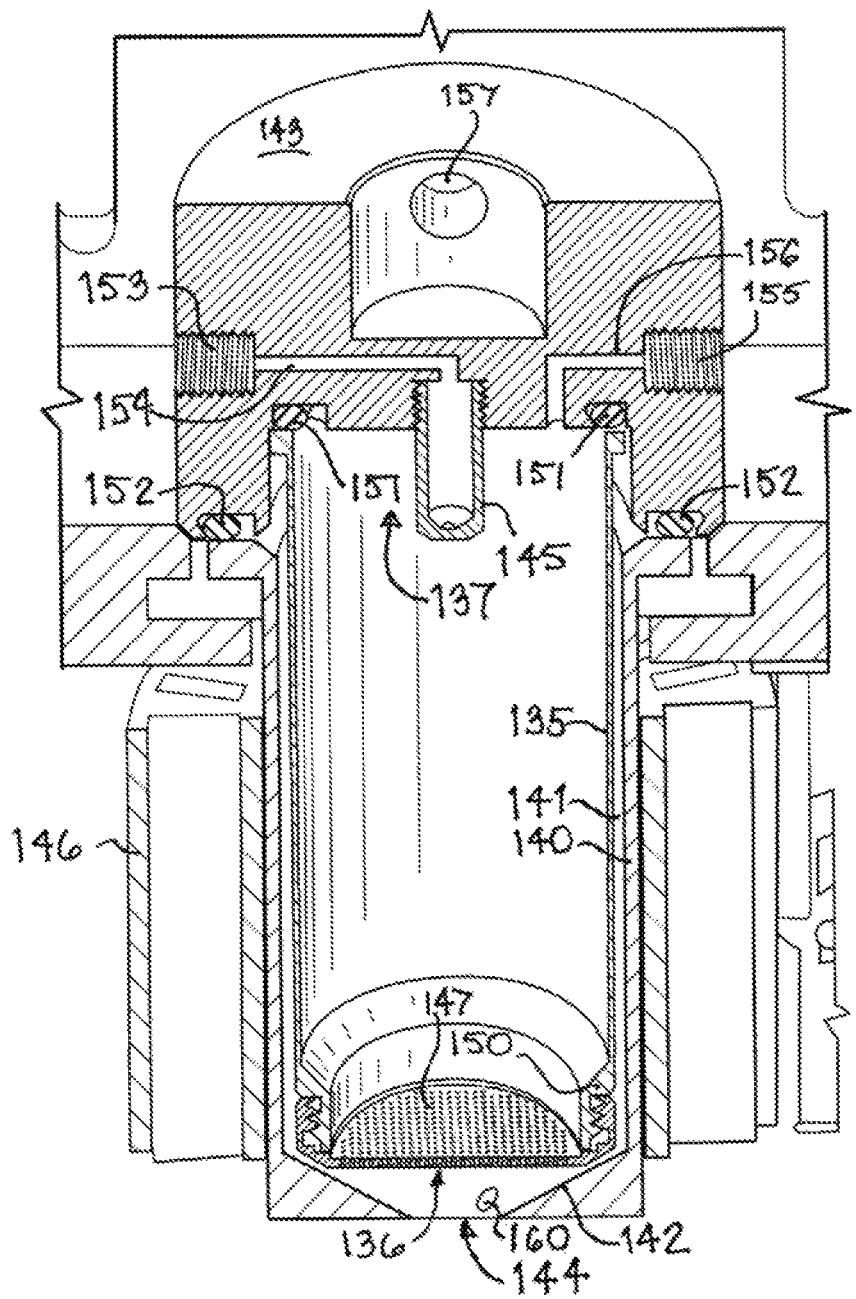
FIG. 20 is a cross-sectional view of portions of the sample cup and the reaction chamber and associated elements.

With that in mind, the embodiment illustrated in FIG. 20 includes a sample cup 135 with one open filtered end 136 and a mouth 137 opposite the open filtered end 136. As used herein, the term opposite certainly includes positions that are diametrically opposed along an axis, but also can mean positions that are situated with the greater part of the sample cup lining between the mouth 137 and the open filtered end 136. See, e.g., Urdang, THE RANDOM HOUSE COLLEGE DICTIONARY, Random House Inc. (1972). The sample cup 135 is cylindrical, and formed of a material with a relatively high heat conductivity, and that withstands vapor pressures generated by typical extraction solvents at temperatures of at least about 125° C., with stainless steel being exemplary. The selection of the appropriate stainless steel (or other alloy or alternative thermally-conductive material) is well within the knowledge of the person of ordinary skill in these arts, and can be selected and incorporated without undue experimentation.

In particular, the cylinder walls of the sample cup 135 can be relatively thin for enhancing heat conduction, provided the walls have sufficient strength for the overall purposes of the instrument and the related methods.

A reaction chamber 140 surrounds the sample cup 135. The reaction chamber 140 and the sample cup 135 are positioned relative to one another to together define open jacket portions 141 between the interior surfaces of the reaction chamber 140 and the exterior surfaces of the sample cup 135. The reaction chamber 140 is likewise formed of a material with a relatively high beat conductivity and physical strength, with those materials that are suitable for the sample cup 135 being similarly suitable for the reaction chamber.

The reaction chamber 140 includes a drain floor 112 which corresponds to the drain 110 illustrated in (for example) FIG. 14. A pressure sealing lid 143 is positioned over the mouth 137 of the sample cup 135 and a first solvent inlet 145 opens from the pressure sealing lid 143 to the interior of the sample cup 135. The drain floor 142 is illustrated as frustoconical in shape, but other shapes (e.g., hemispherical, polygonal) are likewise appropriate, provided the solvent drains as intended.

A second solvent inlet 141 provides fluid communication through and between the drain floor 142 and the reaction chamber 140 and external waste containers or solvent sources.

A reaction chamber heater 146 is positioned in thermal contact with the reaction chamber 140. In this arrangement solvent (e.g., from the tank 165 in FIG. 24) can be added from two directions. First, solvent can be added to the sample cup from the first solvent inlet 145 into the sample cup 135. Additionally solvent can be added from the second inlet 144 into both the jacket portions 141 and (through the open filtered end 136 and the foraminous floor 147) into the sample cup 135 so that the reaction chamber heater 146 can heat the reaction chamber 140 and solvent in the jacket portions 141, which in the embodiment illustrated in FIG. 20 form a cylinder between the cylindrical reaction chamber 140 and the cylindrical sample cup 135.

In turn the heated solvent in the jacket portions 141 can heat the sample cup 135 and heat solvents and extraction samples inside the sample cup 135.

FIG. 20 also illustrates that in this embodiment the open filtered end 130 of the sample cup 135 is a threaded foraminous floor 147 analogous to the foraminous floor 96 (FIG. 8). The lower end of the sample cup 135 likewise carries threads 150 so that the foraminous floor can be removed from the sample cup 135, typically to remove a filter medium (148, FIG. 24) from lower portions of the sample cup 135. Typically the filter medium rests on the foraminous floor 147, and can be formed of a disk or equivalent, shape of filter paper, quartz fiber filters, membrane filters, filtration microplates, or any oilier filler medium (or media, or combinations) that are otherwise consistent with the chemistry of the samples, the solvents, and the expected or desired flow rate of solvents from the sample cup 135 following a heated extraction.

FIG. 20 also illustrates that the sample cup 135 can be sealed to the pressure sealing lid 143 with the aid of an O-ring 151 and that the entire reaction chamber 140 can be pressure sealed with the aid of a larger O-ring 152.

The first solvent inlet 145 communicates with any convenient solvent source (165, FIG. 24) through the threaded inlet fitting 153 and its tube 154 both of which are part of the pressure sealing lid 143. Another portion of the pressure sealing lid 143 includes a female threaded opening 155 and its associated tube 156, the combination of which serves at least two useful purposes when using the instrument 30 and carrying out heated extractions. First, the opening 155 can be used to vent the reaction vessel 135 as desired or necessary. More specifically to associated extraction methods, the opening 155 can be attached to a valve (138, FIG. 24)) which in turn can control the flow of gases into and out of the sample cup 135 as well as to any associated pressure gauge (139, FIG. 24).

As additional details, FIG. 20 illustrates a tool seat 157 in the lid 143 for assisting in opening the entire reaction chamber 140. A thermocouple (shown schematically at 160) is positioned in or near the drain floor 142 in order to provide a highly accurate temperature measurement of the sample cup 135 and any extraction sample and solvent in the sample cup 135.

The benefits of the thermocouple 160 and the pressure gauge 139 are more evident in the context of the method described later herein.

As in the earlier-presented embodiments, the instrument 30 includes a chiller 130 in liquid communication with the drain floor 142 in the sample cup 135 for receiving heated liquids from the sample cup at 135 and the reaction chamber 140 when the drain floor 142 is opened (again using a valve) to atmospheric pressure. As in the previously illustrated embodiments, the chiller 130 is a cooling coil in liquid communication with the drain floor 142, and the cooling coil 130 has a length sufficient to reduce the temperature of common extraction solvents from between about 120° C. and 130° C. to between about; 25° C. and 35° C. as the solvent travels the length of the cooling coil 130.

Figure 21:
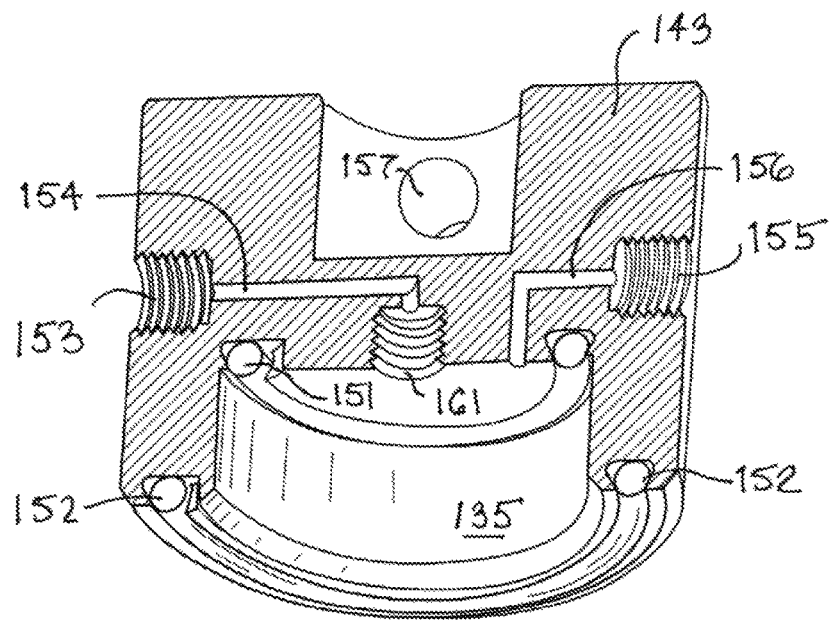
FIG. 21 is a partial cross-sectional and partial perspective view of portions of the reaction chamber.
Figure 22:
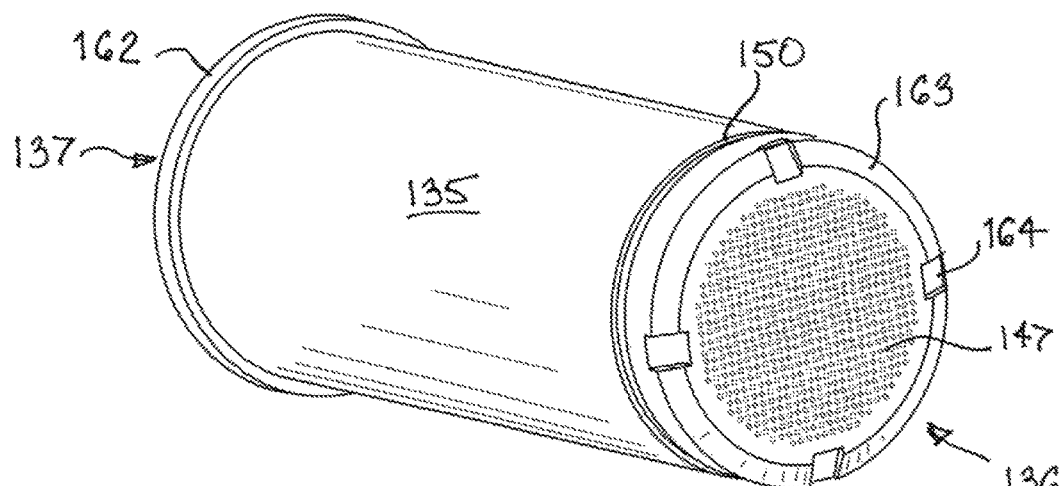
FIG. 22 is a perspective view of an exemplary sample cup.
Figure 23:
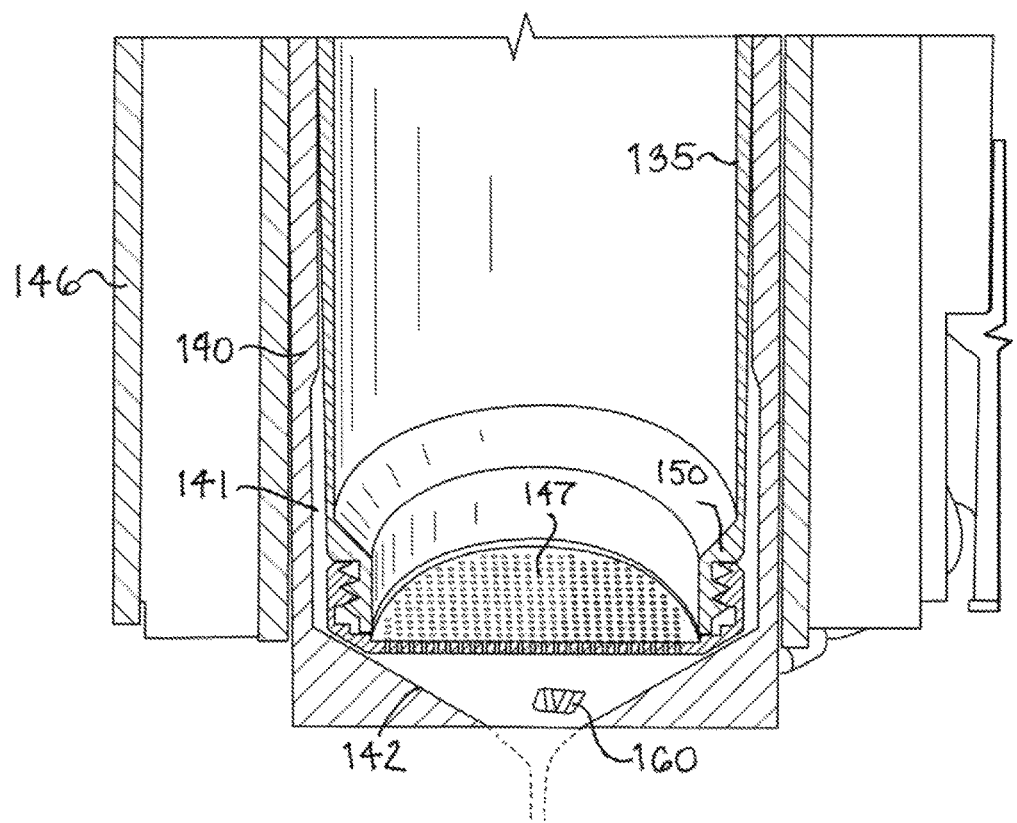
FIG. 23 is an enlarged cross-sectional view of lower portions of the sample cup in the reaction chamber.
Figure 24:
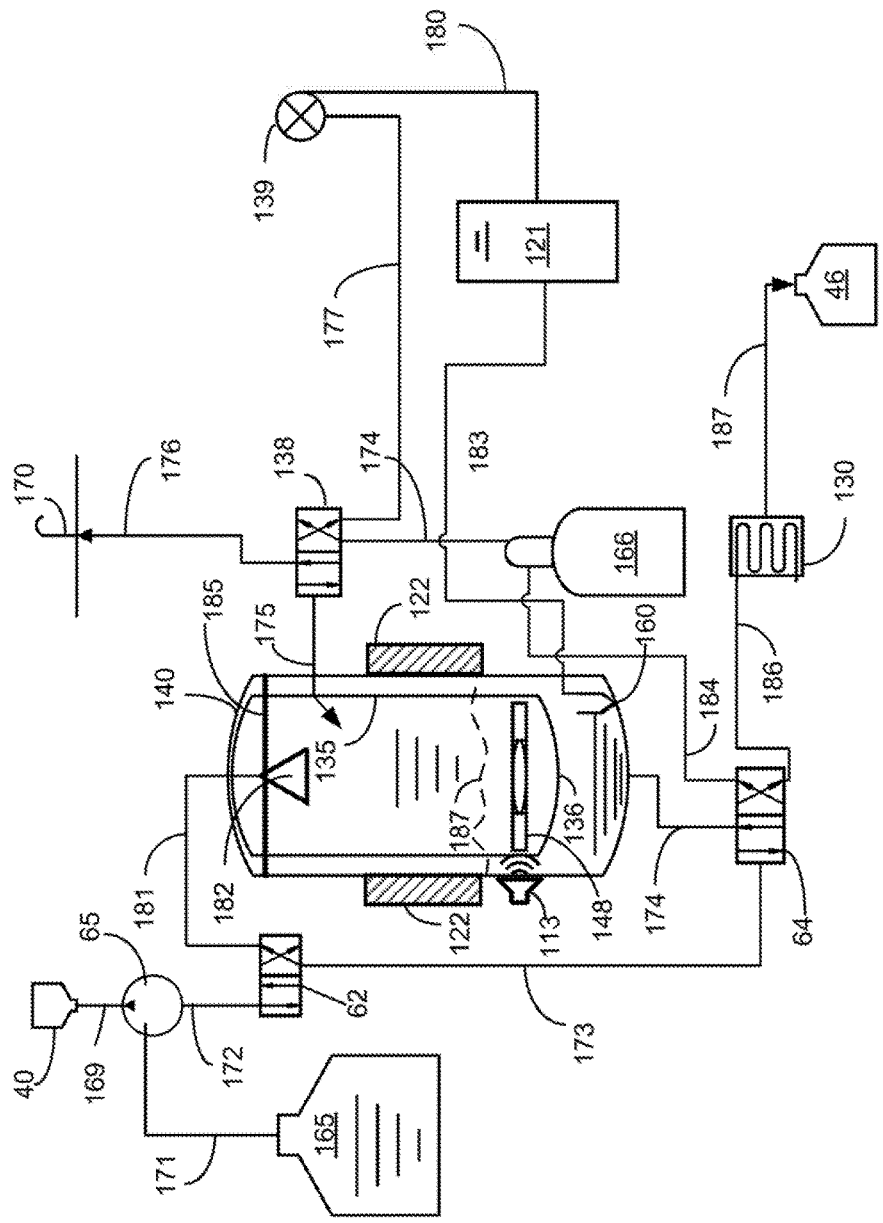
FIG. 24 is a schematic diagram illustrating the relevant fluid circuitry for liquids and gases.

FIGS. 21, 22, and 23 illustrate the same elements as FIG. 20, but in either in larger or separated detail. In FIG. 21 such details include the threads 161 for the first solvent inlet 145, with the remaining elements otherwise being the same as in FIG. 20 and numbered accordingly.

FIG. 22 is an isolated perspective view of the sample cup 135 with the threaded foraminous floor 147 shown in place on the male threaded end 150 of the sample cup 135. FIG. 22 illustrates that the sample cup 135 has a mouth lip 162 and a beveled edge 163 on the threaded foraminous floor 147 that helps seat the threaded foraminous floor 147 in the drain floor 142.

In order to allow solvent to flow from the drain floor 142 into the jacket portions 141, the threaded fora ruinous floor 147 also carries a plurality (four are shown) of seal breaks illustrated as the notches 164.

The embodiment illustrated in FIGS. 20-23 provides the capability to carry another helpful method embodiment. In this context, the invention is an extraction method comprising the steps of placing an extraction sample in the heat conductive sample cup 135 surrounded by the reaction chamber 140 with the heat conductive sample cup 135 having its open filtered end 136, and then adding extraction solvent to both the inside of the sample cup 135 and to the reaction chamber 140 outside of the sample cup 135.

Heating the solvent in the reaction chamber 140 outside of the sample cup 135 in turn heats the sample cup 135, heats the solvent inside the sample cup 135, and heats the extraction sample inside the sample cup 135. In particular, the method heats solvent outside of the sample cup 135 by heating the reaction chamber 140.

In the method, the extraction solvent is added to the sample cup 135 through the open filtered end 136 to thereby help agitate the extraction sample with the extraction solvent.

Using the illustrated embodiment of the instrument 30, the extraction method further comprises sealing the sample cup 135 between the pressure seating lid 143 at the sample cup mouth 137 and the outlet valve 138 in fluid communication with the open filtered end 136 of the sample cup 135 so that the heating step increases the vapor pressure of the extraction solvent above the solvent's vapor pressure at standard temperature and pressure (25° C.; 1 atmosphere).

Opening the outlet valve 138 allows the vapor pressure in the sample cup 135 to drive the extraction solvent out of the sample cup 135 through the open filtered end 136, to the drain floor 142 and through the outlet valve 138.

As set forth with respect to the description of the physical parts, the method typically includes the step of driving the solvent into the chiller 130 for a time sufficient to reduce the temperature of common extraction solvents from between about 120° C. and 130° C. to between about 25° C. and 35° C. in the chiller (coil) 130.

Finally, the extraction solvent can be collected from the coil 130 for molecular analysis.

The embodiment illustrated in FIGS. 20-23 accordingly describes an instrument that incorporates the extraction solvent itself for additional thermal conduction as well as extraction. The capacity to pressure-seal the sample cup in the chamber helps increase the vapor pressure for those solvent-sample combinations where this is helpful or necessary.

The combination of the thermocouple 160 and the pressure gauge 139 can be used to accurately determine the temperature in the sample cup 135 in relation to the vapor pressure of the selected extraction solvent. In particular, the embodiment illustrated in FIGS. 23-20 can be used to run a solvent or solvent system alone in the instrument to develop a correlation between solvent temperature and vapor pressure. As schematically illustrated in FIG. 24, a processor 149 can be used for this purpose. Thereafter, vapor pressure can be measured to indicate solvent temperature in the sample cup 135 with a high degree of accuracy.

As a further advantage, Because this embodiment seals the sample cup 135 in the reaction chamber 140, the system can also be pre-pressurized (for example up to about 25 pounds per square inch) in the headspace (i.e., the gas above the solvent and sample) with air or an inert gas (i.e., a gas inert to the sample and to the extraction solvent; 166 in FIG. 24) to help force the hot liquid solvent to a higher temperature before the solvent generates the desired vapor pressure. Keeping the solvent in the liquid state also helps with the desired the thermal transfer inside and outside of the reaction vessel.

A gas valve 167 can vent the system (e.g., to vent 170 in FIG. 24), or direct gas for pressure measurement at the gauge 139, or direct inert gas from the source 166 into the reaction vessel 135.

Perhaps just as importantly, a higher pressure in the headspace helps ensure that all of the extraction solvent is pushed from the sample cup 135, through any filter media and the foraminous floor 147, and thereafter to the drain floor 142 and the cooling coil 130.

Further to FIG. 24 and to complete the description of the possibilities, solvent can flow from the solvent supply 165 to the rotary valve 65 through the line 171. The line 172 connects the rotary valve 65 with the auxiliary valve 62. The line 173 connects the auxiliary valve 62 to the gas valve 64 which in turn can use the line 174 to deliver solvent to the bottom of the reaction chamber 140.

The line 169 connects the rotary valve 65 to the syringe 40 so that liquids from the supply 165 can be metered into the syringe 40 from the supply 165 and thereafter from the syringe 40 into the sample cup and through the lines 172 and 181 and the dispenser head 182. The dotted line 187 represents the position of solvent between the sample cup 135 and the reaction chamber 140 when the solvent is used to jacket the sample cup 135.

The gas supply 166 can supply extra pressure to the headspace through the lines 174 and 175 which, along with the gas flow to several other items, is controlled by the valve 138. The line 176 joins the valve 138 to the vent 170.

As part of the gas pressure monitoring, the line 177 connects the valve 138 to the pressure gauge 139 and the pressure gauge 139 is wired to the processor 121 through the communication line 180. The processor 121 is also connected to the thermocouple 160 using the communication line 183 so that monitored combinations of temperature and vapor pressure for various sample extractions can he used to develop helpful standardized information.

In order to provide agitating gas into the bottom of the reaction chamber 140 and the sample cup 135, the gas supply at 166 is also connected to the valve 64 through an appropriate line or lube 184.

A pressure head seal 185 seals the sample cup in the reaction chamber. Line 186 drains solvent from the valve 64 to the coil 130, and line 187 drains front the coil 130 to the collection vessel 46.

In the drawings and specification there has been set forth a preferred embodiment of the invention, and although specific terms have been employed, they are used in a generic and descriptive sense only and not for purposes of limitation, the scope of the invention being defined in the claims.

The invention claimed is:

1. A sample preparation instrument that is particularly suitable for extraction related techniques, said instrument comprising:
    a sample cup with one opened filtered end and a mouth opposite said filtered end;
    a reaction chamber surrounding said sample cup, said reaction chamber and said sample cup defining open jacket portions between the interior surfaces of said reaction chamber and exterior surfaces of said sample cup, with said reaction chamber including,
    a drain floor in communication with said opened filtered end of said sample cup and in communication with said open jacket portions;
    a pressure sealing lid over said mouth of said sample cup;
    a first solvent inlet from said pressure sealing lid to the interior of said sample cup; and
    a second solvent inlet from said drain floor into said reaction chamber; and
    a reaction chamber heater in thermal contact with said reaction chamber;
    so that solvent can be added from both of the first and second solvent inlets into said sample cup and from said second solvent inlet into said jacket portions so that said heater can heat said reaction chamber and solvent in said jacket portions, and so that heated solvent in said jacket portions can heat said sample cup and heat solvents and extraction samples inside said sample cup and so that solvent from said second inlet can enter said sample cup through said open filtered end and favorably agitate extraction solvents and samples in said sample cup.

2. A molecular sample preparation instrument according to claim 1 further comprising a chiller in liquid communication with said drain floor in said sample cup for receiving heated liquids from said reaction chamber when said drain floor is opened to atmospheric pressure.

3. A molecular sample preparation instrument according to claim 2 wherein said chiller is a cooling coil in liquid communication with said drain floor, said cooling coil having a length sufficient to reduce the temperature of common extraction solvents from between about 50° C. and 180° C. to between about 25° C. and 40° C. as the solvent travels the length of said cooling coil.

4. A molecular sample preparation instrument according to claim 1 wherein said sample cup is a cylinder and said open filtered end is a foraminous floor.

5. A molecular sample preparation instrument according to claim 4 in which said foraminous floor and said sample cup are threaded for removal of said foraminous floor.

6. A molecular sample preparation instrument according to claim 1 and further comprising:
    a filter medium resting on said foraminous floor in said sample cup;
    with said filter medium being selected from the group consisting of filter paper, quartz fiber filters, membrane filters, and filtration microplates.

\* \* \* \* \*

UNITED STATES PATENT AND TRADEMARK OFFICE
CERTIFICATE OF CORRECTION

PATENT NO. : 10,241,014 B2
APPLICATION NO. : 15/644938
DATED : March 26, 2019
INVENTOR(S) : Michael J. Collins, Sr. et al.

It is certified that error appears in the above-identified patent and that said Letters Patent is hereby corrected as shown below:

On the Title Page

Item (57), in the ABSTRACT on Line 5:
Delete: "healing"
And INSERT: --heating--

On Page 2, item (56), under FOREIGN PATENT DOCUMENTS:
Delete: "GB 583121"
And INSERT: --GB 683121--
Delete: "GB 345131"
And INSERT: --GB 845131--

On Page 2, item (56), under OTHER PUBLICATIONS:
Delete: "Thei Basics"
And INSERT: --The Basics--

In the Specification

Column 1, Line 26:
Delete: "slops,"
And INSERT: --steps,--

Column 1, Line 65:
Delete: "safely"
And INSERT: --safety--

Column 2, Line 17:
Delete: "healing"
And INSERT: --heating--

Signed and Sealed this
Fourth Day of June, 2019

Andrei Iancu
*Director of the United States Patent and Trademark Office*

CERTIFICATE OF CORRECTION (continued)
U.S. Pat. No. 10,241,014 B2

Column 3, Line 12:
Delete: "anal vie"
And INSERT: --analyte--

Column 3, Line 36:
Delete: "belter"
And INSERT: --better--

Column 3, Line 60:
Delete: "band"
And INSERT: --hand--

Column 4, Line 52:
Delete: "healing"
And INSERT: --heating--

Column 5, Line 1:
Delete: "front"
And INSERT: --from--

Column 5, Line 52:
Delete: "a long"
And INSERT: --along--

Column 6, Line 49:
Delete: "30"
And INSERT: --36--

Column 8, Line 42:
Delete: "press urination."
And INSERT: --pressurization--

Column 11, Line 10:
Delete: "Held."
And INSERT: --field.--

Column 11, Line 13:
Delete: "solvent,"
And INSERT: --solvent--

Column 12, Line 31:
Delete: "healed"
And INSERT: --heated--

CERTIFICATE OF CORRECTION (continued)
U.S. Pat. No. 10,241,014 B2

Column 12, Line 64:
Delete: "adds,"
And INSERT: --acids,--

Column 13, Line 17:
Delete: "Environnmental"
And INSERT: --Environmental--

Column 13, Line 45:
Delete: "80"
And INSERT: --86--

Column 13, Line 51:
Delete: "Extracton"
And INSERT: --Extraction--

Column 14, Line 24:
Delete: "2-methylnaphthalone."
And INSERT: --2-methylnaphthalene.--

Column 14, Line 59:
Delete: "oft"
And INSERT: --off--

Column 16, Line 56:
Delete: "lining"
And INSERT: --being--

Column 17, Line 11:
Delete: "beat"
And INSERT: --heat--

Column 17, Line 15:
Delete: "112"
And INSERT: --142--

Column 17, Line 24:
Delete: "141"
And INSERT: --144--

Column 17, Line 45:
Delete: "130"
And INSERT: --136--

CERTIFICATE OF CORRECTION (continued)
U.S. Pat. No. 10,241,014 B2

Column 17, Line 54:
Delete: "oilier filler"
And INSERT: --other filter--

Column 18, Line 46:
Delete: "fora ruinous"
And INSERT: --foraminous--

Column 19, Line 3:
Delete: "seating"
And INSERT: --sealing--

Column 19, Line 32:
Delete: "23-30"
And INSERT: --23-26--

Column 20, Line 17:
Delete: "he"
And INSERT: --be--

Column 20, Line 22:
Delete: "lube"
And INSERT: --tube--

Column 20, Line 25:
Delete: "front"
And INSERT: --from--